US007158862B2

(12) United States Patent
Liebler et al.

(10) Patent No.: US 7,158,862 B2
(45) Date of Patent: Jan. 2, 2007

(54) METHOD AND SYSTEM FOR MINING MASS SPECTRAL DATA

(75) Inventors: Daniel C. Liebler, Tucson, AZ (US); Beau T. Hansen, Tucson, AZ (US); Daniel E. Mason, Tucson, AZ (US); Sean W. Davey, Tucson, AZ (US); Juliet A. Jones, Tucson, AZ (US); Thomas McClure, Santee, CA (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 471 days.

(21) Appl. No.: 09/877,182

(22) Filed: Jun. 11, 2001

(65) Prior Publication Data

US 2002/0023078 A1 Feb. 21, 2002

Related U.S. Application Data

(60) Provisional application No. 60/210,981, filed on Jun. 12, 2000.

(51) Int. Cl.
*G06F 19/00* (2006.01)
*B01D 59/44* (2006.01)
*G01N 33/50* (2006.01)

(52) U.S. Cl. ...................... 700/266; 250/281; 250/282; 422/62; 436/86; 436/94; 436/173; 700/273; 702/19; 702/20; 702/22; 702/23; 702/27

(58) Field of Classification Search .................. 436/86, 436/94, 173; 700/266, 273; 422/62; 702/19–20, 702/27, 22–23; 250/281–282
See application file for complete search history.

(56) References Cited

U.S. PATENT DOCUMENTS

| | | | | |
|---|---|---|---|---|
| 5,453,613 | A * | 9/1995 | Gray et al. | 250/281 |
| 5,538,897 | A | 7/1996 | Yates, III et al. | |
| 5,545,895 | A | 8/1996 | Wright et al. | |
| 5,701,400 | A * | 12/1997 | Amado | 706/45 |
| 5,900,634 | A * | 5/1999 | Soloman | 250/339.11 |
| 6,017,693 | A * | 1/2000 | Yates et al. | 435/5 |

(Continued)

FOREIGN PATENT DOCUMENTS

WO 99/62930 * 12/1999

OTHER PUBLICATIONS

Burlingame, A. L. et al, Analytical Chemistry 1968, 40, 13-19.*

(Continued)

*Primary Examiner*—Arlen Soderquist
(74) *Attorney, Agent, or Firm*—Oblon, Spivak, McClelland, Maier & Neustadt, P.C.

(57) ABSTRACT

A method, system, and computer program product for mining mass spectral data to detect chemical-specific characteristic features in large databases and/or files, including specifying spectral characteristics of mass spectra to mine, specifying a relationship between the spectral characteristics, searching the mass spectra for portions of the mass spectra which match the spectral characteristics based on the relationship, and assigning scores to the portions of mass spectra to indicate a degree of correlation between the portions of mass spectra and the spectral characteristics. Exemplary embodiments encompass a user specification of the spectral characteristics and their relationships used to mine the mass spectral data, automated specification of the spectral characteristics and their relationships used to mine the data, and real-time data mining wherein the mass spectrometer is adjusted based on the result.

48 Claims, 25 Drawing Sheets

U.S. PATENT DOCUMENTS 6,453,242 B1 * 9/2002 Eisenberg et al. ............ 702/19
6,624,408 B1 * 9/2003 Franzen ...................... 250/282

OTHER PUBLICATIONS

Venkataraghavan, R. et al, Organic Mass Spectrometry 1969, 2, 1-15.*
Smith, D. H. Analytical Chemistry 1972, 44, 536-547.*
Kwok, K.-S. et al, Journal of the American Chemical Society 1973, 95,4185-4194.*
Dromey, R. G. Analytical Chemistry 1976, 48, 1464-469.*
Hollos, J. Magyar Kemiai Folyoirat 1976, 82, 512-513.*
Damen, H. et al, Analytica Chimica Acta 1978, 103, 289-302.*
Rasmussen, G. T. et al, Journal of Chemical Information and Computer Sciences 1979, 19, 98-104.*
Mun, In Ki et al, Analytical Chemistry 1981, 53, 179-182.*
Brotherton, H. O. et al, Analytical Chemistry 1983, 55, 549-553.*
Hines, W. M. et al, Journal of the American Society for Mass Spectrometry 1992, 3, 326-336.*
Yates, J. R., III et al, Analytical Biochemistry 1993, 214, 397-408.*
Eng, J. K. et al, Journal of the American Society for Mass Spectrometry 1994, 5), 976-989.*
Mann, M. et al, Analytical Chemistry 1994, 66, 4390-4399.*
Fang, H. et al, Shengwu Huaxue Yu Shengwu Wuli Jinzhan 1995, 22, 361-366.*
Yates, J. R., III et al, Analytical Chemistry 1995, 67, 1426-1436.*
Stein, S. E. Journal of the American Society for Mass Spectrometry 1995, 6, 644-655.*
McLuckey, S. A. et al, Journal of Mass Spectrometry 1995, 30, 1222-1229.*
Yates, J. R., III et al, Analytical Chemistry 1995, 67, 3202-3210.*
Bonner, R. et al, Rapid Communications in Mass Spectrometry 1995, 9, 1077-1080.*
Qian, M. G. et al, Rapid Communications in Mass Spectrometry 1996, 10, 1209-1214.*
Windig, W. et al, Analytical Chemistry 1996, 68, 3602-3606.*
Fernandez-de-Cossio, J. et al, Rapid Communications in Mass Spectrometry 1998, 12, 1867-1878.*
Fleming, C. M. et al, Journal of Chromatography, A 1999, 849, 71-85.*
Tong, H. et al, Journal of the American Society for Mass Spectrometry 1999, 10, 1174-1187.*
Gras, R. et al., Electrophoresis 1999, 20, 3535-3550.*
Moore, R. E. et al, Journal of the American Society for Mass Spectrometry 2000, 11, 422-426.*
Kundred, A. et al, Analytical Chemistry 1971, 43, 1086-1090.*
Abramson, F. P. Analytical Chemistry 1975, 47, 45-49.*
Kwiatkowski, J. et al, Analytica Chimica Acta 1979, 112, 219-231.*
Domokos, L. et al, Analytica Chimica Acta 1984, 165, 61-74.*
McLafferty, F. W. et al, Journal of Chemical Information and Computer Sciences 1985, 25, 245-252.*
Wade, A. P. et al, Analytica Chimica Acta 1988, 215, 169-186.*
Zhu, D. et al, Analyst 1988, 113, 1261-1265.*
Loh, S. Y. et al, Analyical Chemistry 1991, 63, 546-550.*
Henneberg, D. et al, Organic Mass Spectrometry 1993, 28, 198-206.*
Taylor, J. A. et al, Rapid Communications in Mass Spectrometry 1997, 11, 1067-1075.*
Lebedev, K. S. et al, Journal of Chemical Information and Computer Sciences 1998, 38, 410-419.*
Wilkins, M. R. et al, Journal of Molecular Biology 1999, 289,,645-657.*
Lennon, J. J. et al, Protein Science 1999, 8, 2487-2493.*
Cross, K. P. et al, ACS Symposium Series 1986, 306, 321-336.*
Cross, K .P. et al, Computers & Chemistry 1986, 10, 175-181.*
Curry, B., ACS Symposium Series 1986, 306, 350-364.*
Neudert, R. et al, Organic Mass Spectrometry 1987, 22, 321-329.*
Pucci, P. et al, Biomedical & Environmental Mass Spectrometry 1988, 17, 287-291.*
Hong, Q. et al, Fenxi Huaxue 1992, 20, 1117-1120.*
Scsibrany, H. et al, Fresenius' Journal of Analytical Chemistry 1992, 344, 220-222.*
Varmuza, K. et al, Laboratory Automation and Information Management 1996, 31, 225-230.*

* cited by examiner

1400

| Score | Precursor m/z | Z Est. Ratio | R.T. (min.) | Scan #'s | Ion |
|---|---|---|---|---|---|
| 012.14 | 0515.08 | 0.57 | 76.82-76.89 | 2179-2181 | Ion Series: 147.01--438.18--567.24 |
| 007.20 | 1028.40 | 0.02 | 76.95-77.03 | 2183-2185 | Ion Series: 438.23--567.29--714.21 |
| 005.28 | 0560.65 | 0.41 | 71.47-71.54 | 2027-2029 | Ion Series: 210.92--374.07--502.97 |
| 005.05 | 1057.21 | 0.69 | 121.76-121.84 | 3411-3413 | Ion Series: 1398.32--1251.37--958. |
| 003.55 | 1184.04 | 0.45 | 131.97-132.04 | 3687-3689 | Ion Series: 1200.67--1328.62--149 |
| 003.46 | 0866.33 | 0.31 | 48.29-48.37 | 1371-1373 | Ion Series: 382.23--510.10--673.86 |
| 003.44 | 0750.14 | 0.65 | 130.29-130.37 | 3639-3641 | Ion Series: 315.33--606.91--736.05 |
| 003.38 | 0546.80 | 0.50 | 67.65-67.72 | 1919-1921 | Ion Series: 359.22--506.33--619.16 |
| 003.33 | 1247.68 | 0.49 | 131.27-131.35 | 3667-3669 | Ion Series: 1200.67--1328.67--149 |
| 003.20 | 0993.64 | 0.46 | 120.06-120.14 | 3367-3369 | Ion Series: 814.40--1090.61--1203. |
| 003.12 | 0423.89 | 0.61 | 61.85-61.92 | 1755-1757 | Ion Series: 309.37--585.34--698.42 |
| 002.88 | 0717.59 | 0.02 | 40.22-40.29 | 1147-1149 | Ion Series: 310.12--439.19--585.92 |
| 002.59 | 0934.75 | 0.53 | 79.67-79.75 | 2259-2261 | Ion Series: 779.61--1055.60--1169. |
| 002.56 | 0608.61 | 0.39 | 61.43-61.50 | 1743-1745 | Ion Series: 544.40--691.54--804.47 |
| 002.38 | 0751.56 | 0.65 | 68.80-68.88 | 1951-1953 | Ion Series: 416.42--544.88--707.75 |
| 002.37 | 0571.50 | 0.50 | 67.08-67.15 | 1903-1905 | Ion Series: 463.28--610.34--723.38 |
| 002.32 | 1110.49 | 0.46 | 126.30-126.39 | 3531-3533 | Ion Series: 1038.03--1201.36--133 |

METHOD AND SYSTEM FOR MINING MASS SPECTRAL DATA

REFERENCE TO PRIOR APPLICATIONS

This application claims benefit of priority under 35 U.S.C. §119(e) to U.S. provisional application Ser. No. 60/210,981, filed on Jun. 12, 2000, the entire contents, including the inventors' papers and the articles cited therein, of which are incorporated herein by reference.

STATEMENT OF FEDERALLY FUNDED RESEARCH

The invention described herein was supported by the National Institutes of Health by Contract No. 1 RO1 ES 10056. The government may have certain rights to this invention.

BACKGROUND OF THE INVENTION

1. Field of the Invention

The present invention generally relates to data processing in the field of data mining and, more particularly, to methods, systems, and computer program products for mining mass spectral data for further analysis.

2. Description of the Background

Mass spectrometry (MS) instruments generate and analyze ions from chemical substances. These analyses yield mass spectra, which reflect the chemical nature of the substances analyzed. MS instruments can generate full-scan mass spectra, which represent all ions generated from chemical substances entering the MS instrument at any particular point in time. MS instruments can also generate tandem mass spectra (MS—MS spectra) by a process in which specific ions are selected (precursor ions) and then subjected to energetic dissociation, which produces fragment ions (product ions). The MS—MS spectrum records the distribution of product ions produced from a specific precursor ion and specific structural features of the precursor species can be deduced from this information. Modern MS instruments are capable of automated acquisition of large numbers of full-scan mass spectra or MS—MS spectra. The automated, high-throughput evaluation of these spectra represents a significant challenge to the utilization of data generated by MS instruments.

Application of modern MS techniques for protein and peptide analysis have made feasible the large-scale analysis of cellular proteomes, which comprise the collection of all proteins in an organism or any subset thereof. Protein components of even highly complex proteomes have been identified by digestion of the proteins to peptides, followed by MS analysis of the peptides. A widely used MS analysis is liquid chromatography coupled to tandem MS (LC-MS—MS) with triple quadrupole, quadrupole-ion trap, quadrupole-time of flight or tandem time of flight MS instruments, which provide useful information in the form of collision-induced dissociation (CID) spectra for peptides. Peptide precursor ions subjected to CID undergo fragmentation to yield product ions, which are recorded in the MS—MS spectra. These spectra contain signals for a variety of product ions, including y-ions, b-ions and related species arising from fragmentation of the peptide backbone. In addition, these MS—MS spectra contain signals indicating the presence and sequence location of peptide modifications.

Identification of peptide sequences from MS—MS spectra may be done by direct interpretation (de novo sequence analysis). Once a peptide sequence has been determined, the source protein may be identified by comparing the peptide sequence to a database of protein sequences. However, typical LC-MS-MS analyses generate hundreds to thousands of MS—MS spectra. The sheer volume of data thus precludes proteome analysis involving de novo sequence interpretation.

Yates, III et al (U.S. Pat. No. 5,538,897) implemented a computer program to correlate MS—MS data with protein and nucleotide sequences stored in databases. This program correlates MS—MS spectra with database sequences that match the measured mass of the peptide precursor ion. This program thus obviates de novo sequence interpretation and greatly speeds protein identification from MS—MS data.

However, a major problem in proteome analysis is the heterogeneity of proteins due to numerous posttranslational modifications, splice variants, gene polymorphisms and mutations. Indeed, any gene may give rise to multiple protein products. Although the program of Yates, III et al can allow for the presence of certain anticipated modifications, the unpredictable and diverse nature of protein modifications often yields peptides of different masses than those in sequence databases. These unanticipated protein modifications prevent correct protein identifications by this program. These circumstances illustrate the need for data evaluation tools that can detect MS—MS data that correspond to variant peptide forms.

The general problem of detecting and characterizing unanticipated peptide variants remains a significant barrier to comprehensive characterization of complex peptide mixtures.

SUMMARY OF THE INVENTION

Accordingly, one object of this invention is to provide a novel method for mining large amounts of data.

Another object of the present invention is to provide a novel method for mining mass spectral data.

Another object of the present invention is to provide a novel method for specifying spectral characteristics of the mass spectral data to be used for mining the data.

Another object of the present invention is to provide a novel method for specifying a user-defined hierarchy of the spectral characteristics to be used for mining the data.

Another object of the present invention is to provide a novel method for effectively mining unanticipated modifications in the mass spectral data.

These and other objects are accomplished by way of a mass spectral data mining system, method, and computer program product constructed according to the present invention, wherein data patterns are used to analyze large databases and/or files to extract useful data. The data patterns can be used to identify the existence of an item, involving a comparison of parameters against a database. Thus, data mining processes are able to sift through large amounts of data to identify and extract specific patterns specified by either the user or the data mining process.

In particular, according to one aspect of the present invention, there is provided a novel method for mining mass spectra, including the steps of specifying spectral characteristics of the mass spectra to mine, specifying a relationship between the spectral characteristics, searching the mass spectra for portions of the mass spectra which match the spectral characteristics based on the relationship between the spectral characteristics, and assigning scores to the portions of mass spectra to indicate a degree of correlation between the portions and the spectral characteristics.

According to another aspect of the present invention, there is provided a novel system implementing the method of the invention.

According to still another aspect of the present invention, there is provided a novel computer program product, included within a computer readable medium of a computer system, which upon execution causes the computer system to perform the method of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
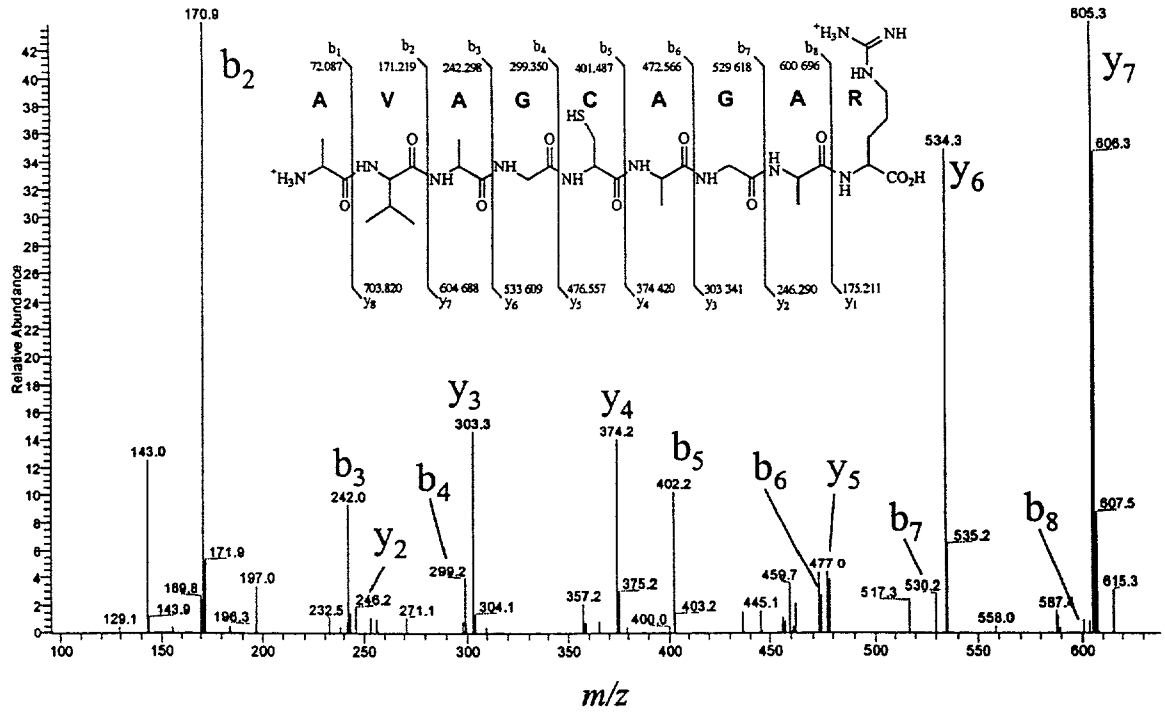
FIG. 1 shows an exemplary mass spectrogram.

Referring now to the drawings, wherein like reference numerals designate identical or corresponding parts throughout the several views, FIG. 1 shows an exemplary MS—MS spectrum produced by CID of the doubly-charged ion of the peptide AVAGCAGAR (alanine-valine-alanine-glycine-cysteine-alanine-glycine-alanine-arginine). This exemplary mass spectrum, also known as a data scan, can be mined according to the present invention to detect chemical-specific characteristic features. In the exemplary mass spectrum, the x-axis indicates mass-to-charge ratio (m/z) of the ion signals detected and the y-axis indicates the relative abundance of particular ions detected by the mass spectrometer. The chemical structure of the peptide is indicated above the mass spectrum and the ion signals in the spectrum are annotated as y-ions and b-ions according to accepted conventions for describing the fragmentation of peptides in CID.

It is to be understood that the mass spectra produced by CID is for exemplary purposes, as mass spectra produced by other techniques can also be mined by the present invention. Such techniques include, but are not limited to, surface-induced dissociation and full-scan MS.

Figure 2:
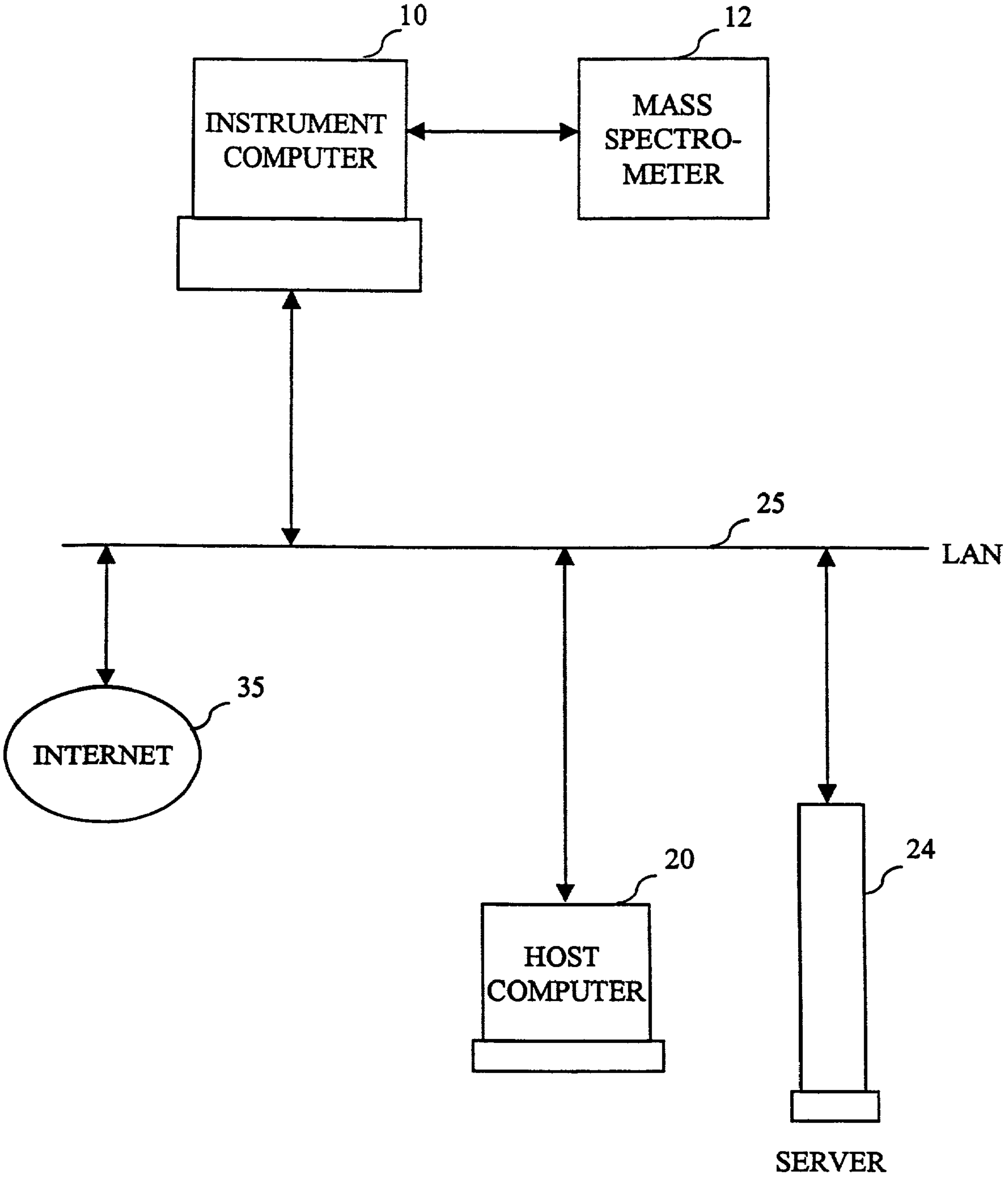
FIG. 2 is a block diagram of a system for mining mass spectral data according to the present invention.

FIG. 2 shows a system for mining mass spectral data. The system includes an instrument computer 10, a mass spectrometer 12, a host computer 20, and a server 24. The mass spectrometer 12 is connected to the instrument computer 10 via a standard data transmission/communication cable and the instrument computer 10, the host computer 20, and the server 24 are connected via a local area network (LAN) 25. The LAN 25 is connected to the Internet 35.

The instrument computer 10 is any suitable computer, workstation, server, or other device for communicating with the host computer 20 and the server 24 via the LAN 25 and other devices via the Internet 35. The instrument computer 10 also sends and receives information to and from the mass spectrometer 12 and controls it.

The mass spectrometer 12 is any suitable chemical analysis device for generating and analyzing ions from chemical substances to be analyzed, for sending information to and receiving control instructions and information from the instrument computer 10.

The host computer 20 is any suitable computer, workstation, server, or other device for communicating with the server 24 and the instrument computer 10 via the LAN 25 and other devices via the Internet 35. The host computer 20 stores data and executes instructions. In the present invention, the host computer 20 stores and performs the steps of the present invention to mine mass spectral data. The host computer 20 sends and receives information to and from the instrument computer 10 and the server 24.

The server 24 is any suitable device for storing and retrieving information to and from the instrument computer 10 and the host computer 20 via the LAN 25 or any other device via the Internet 35. In the present invention, the server 24 stores the mass spectral data from the instrument computer 10 and sends the data to the host computer 20 where the data is mined.

It is to be understood that the system in FIG. 2 is for exemplary purposes only, as many variations of the specific hardware and software used to implement the present invention will be readily apparent to one having ordinary skill in the art. For example, the host computer 20 and the server 24 may be connected to the instrument computer 10 via the Internet 35 rather than by the LAN 25. Or the host computer 20 may be removed and the present invention performed by the instrument computer 10. Or a local database or the instrument computer 10 may be used to store the mass spectral data rather than the server 24.

Figure 3:
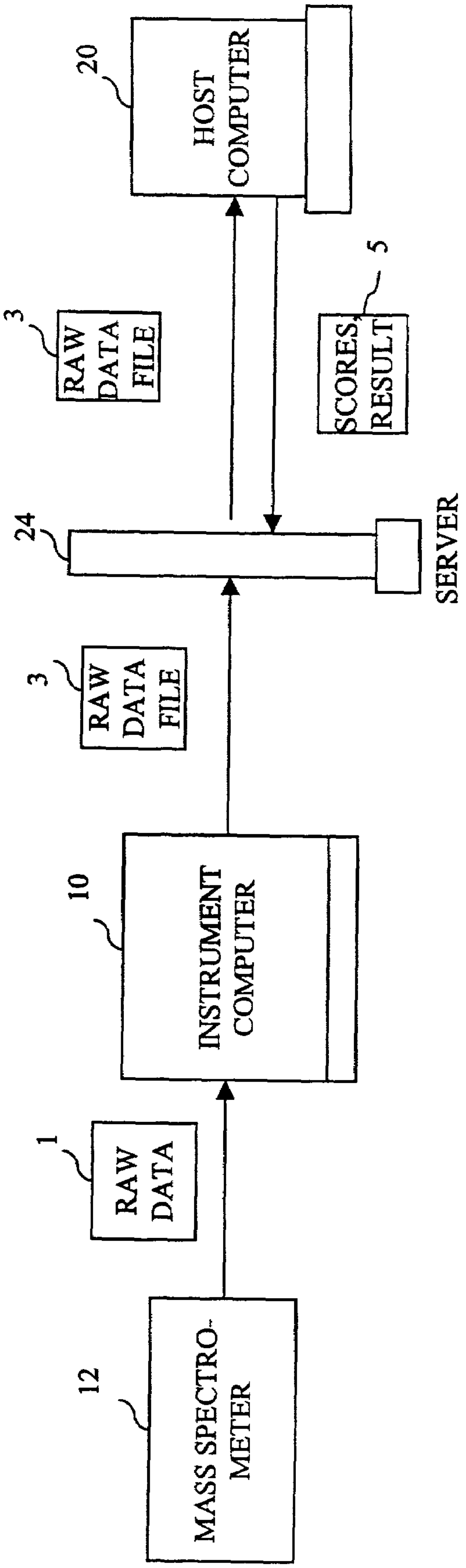
FIG. 3 is an exemplary data flow of mass spectral data according to the present invention.

FIG. 3 shows the data flow performed by the system of FIG. 2 when mining mass spectral data according to the present invention. A chemical sample is analyzed by the mass spectrometer 12 to determine the chemical species in the sample through a series of MS—MS scans producing mass spectral data as raw data 1. Multiple replicate MS—MS scans are acquired for each data sample at the mass spectrometer 12, primarily to get a representative analysis of the sample. Although sets of three MS—MS scans are commonly acquired, any number of scans may be acquired in a set. The mass spectrometer 12 then sends the raw data 1 to the instrument computer 10 which stores the raw data 1 in a data file 3. After the MS—MS scans are completed, the instrument computer 10 sends the data file 3 to the server 24 for storage. The host computer 20 then retrieves the data file 3 from the server 24 and performs data mining on the data file 3 to identify and extract spectral data of interest. Each set of multiple scans is then averaged and all further operations are performed on the averaged scans. In this case, averaging means that an average value is calculated for the signal intensity at each product ion mass per unit charge (hereinafter referred to as m/z) value for the set of scans to be averaged. After completing the mining process, the host computer 20 sends the results and scores 5 to the server 24 for storage.

It is to be understood that the data flow illustrated in FIG. 3 is for exemplary purposes only, as many variations of the specifics may occur corresponding to the many variations available in the system hardware and software.

Figure 4:
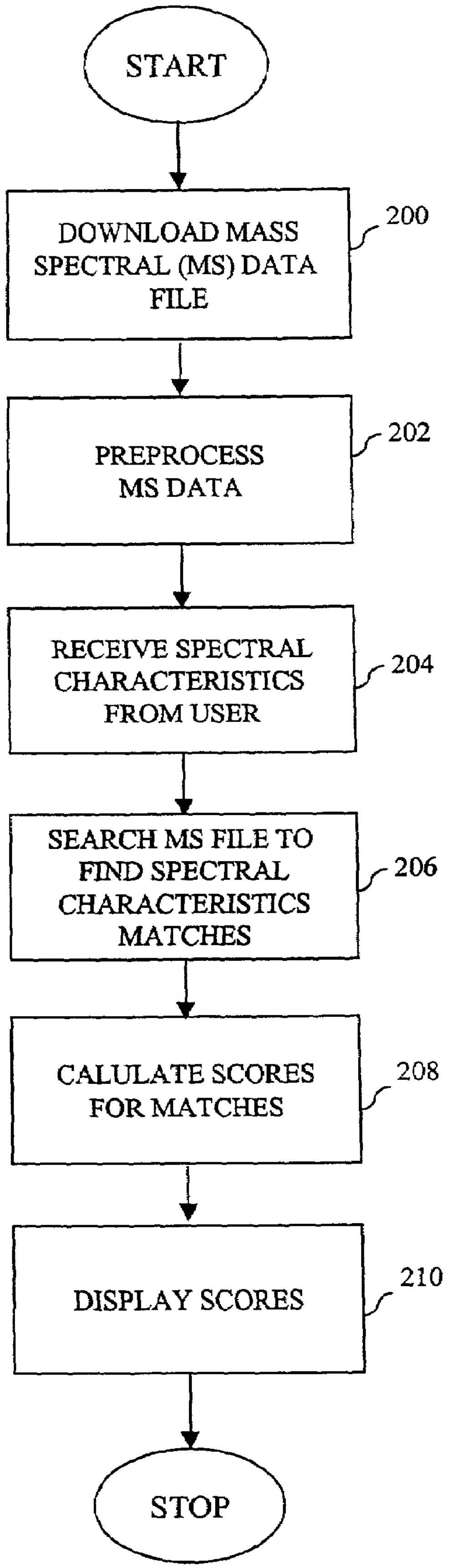
FIG. 4 is a flowchart of an embodiment of the present invention describing a method for mining mass spectral data in which the user specifies the spectral characteristics and the relationship between the spectral characteristics.

FIG. 4 shows one embodiment of a method for mining mass spectral data of the present invention. First, the user starts the method of the present invention. In step 200, the user selects the data file in which to mine and the file is downloaded to the host computer. The host computer then preprocesses the mass spectral data from the downloaded data file in step 202 to subtract nonfragment ions, estimate precursor charge, and normalize ion intensities at a percentage of the total ion current (% TIC). The normalization eliminates bias toward detection of more highly abundant species and permits identification of species present at low concentrations. The user then inputs the spectral characteristics and their relationships to each other in step 204 via a control window, for example. This step allows the user to specify the spectral characteristics and relationships which are most useful in identifying a given chemical species and in effectively detecting unanticipated modifications in the data. The preprocessed spectra are then evaluated to find matches for the specified spectral characteristics in step 206. Scores are then computed by taking into account the % TIC values of the matched ions along with the user-defined hierarchy of spectral characteristics in step 208. The results of the search are then displayed in step 210 in either tabular or graphical form, thereby, providing an easily comprehensible output.

It is to be understood that the user may be a human, a computer program, or any object capable of transmitting instructions causing the method of the present invention to be performed.

Figure 5:
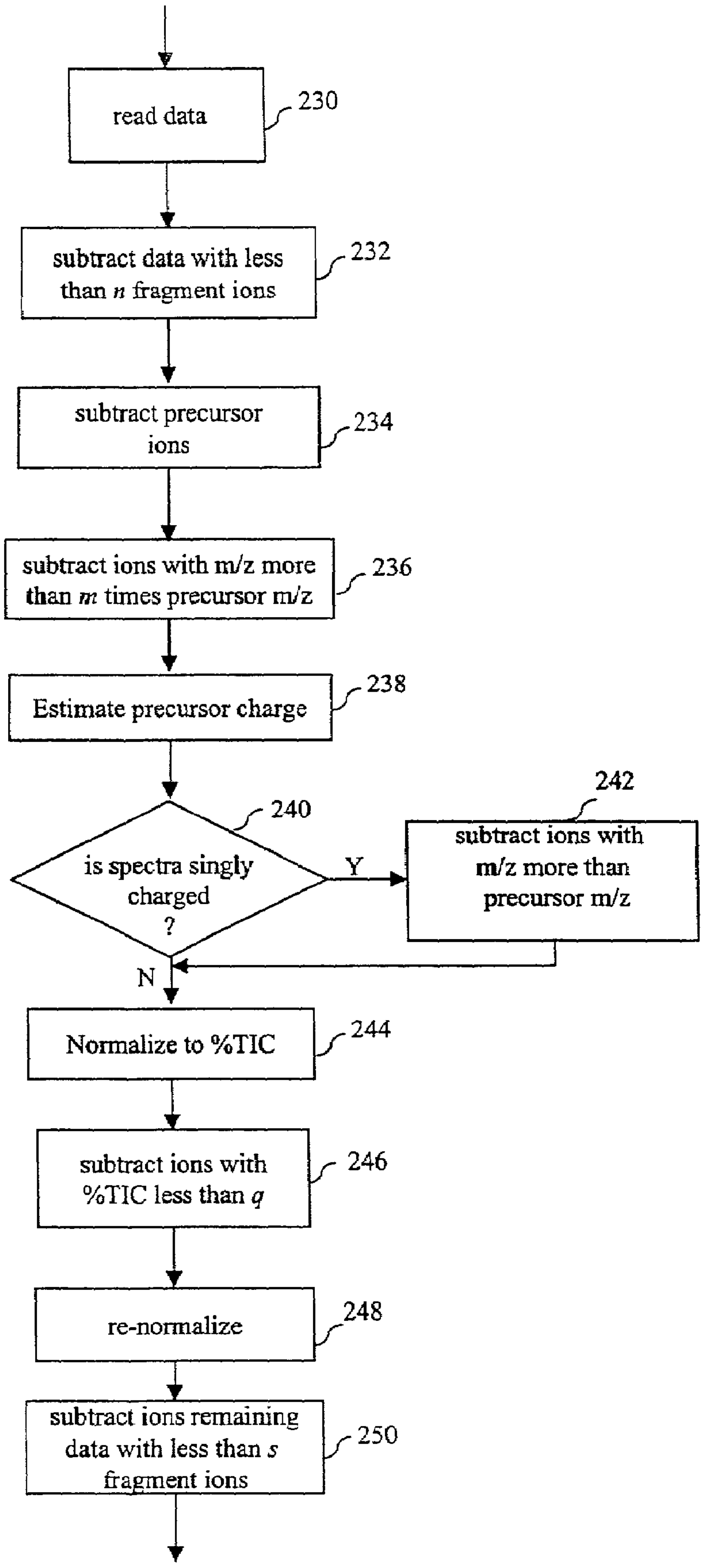
FIG. 5 is a flowchart describing the preprocessing step of the embodiment of FIG. 4.

FIG. 5 shows the steps included in the preprocessing step 202 of FIG. 4. The mass spectral data with at least n fragment ions are preprocessed by a data workup subroutine in which precursor charge is estimated and fragment ions are normalized according to % TIC. In this embodiment, n is set to 25. First, the data is read in step 230 by the host computer. Data with less than n fragment ions are subtracted from the spectra in step 232. In step 234, the precursor ions and ions within ±p % of the specified precursor m/z are subtracted from each spectrum, along with ions with m/z greater than m times that of the precursor ion in step 236. In this embodiment, p is set to 0.4 and m is set to 2. The precursor charge is then estimated by calculating the ratio of the summed ion current for ions with m/z greater than the precursor to the total ion current for the remaining ions in step 238. Spectra with a ratio greater than 0.1 are defined as arising from doubly charged precursors. Spectra with a ratio less than or equal to 0.1 are defined as arising from singly charged precursors, and all ions with m/z greater than the precursor are subtracted from the spectra. So in step 240, an inquiry is made as to whether the spectra are singly or doubly charged. If the spectra are singly charged, then all ions with m/z greater than the precursor are subtracted from the spectra in step 242. Then, in step 244, the remaining fragment ions are normalized to % TIC, where each ion has a value equal to 100×(ion intensity/summed ion intensity of the remaining ions). In step 246, ions with a % TIC value less than q are subtracted from the spectra. In this embodiment, q is set to 0.2. Then, in step 248, the remaining ions are again normalized. The remaining data with less than s fragment ions are subtracted from the spectra in step 250. In this embodiment, s is set to 15. These subtractions maximize the % TIC for fragment ions detected and decrease background noise for ion series (or pair) detection.

FIGS. 6A through 6D illustrate how the matching and scoring in steps 206 and 208, respectively, of FIG. 4 are performed. The spectral characteristics illustrated include product ions, losses of neutral or charged fragments, ion pairs, and ion series.

The product ion spectral characteristic is specified as a m/z value. To match spectra to the specified product ion characteristic, the spectra are searched for ions having this specified m/z value. Then searching is performed within a window centered at the specified m/z value ±b m/z and a most abundant ion $i_1$ in the window is selected. In this embodiment, b is set to 0.5. The product ion match of these spectra is then scored as the % TIC value $I_1$ for the selected ion as follows:

$$Score=I_1 \tag{1}$$

Figure 6A:
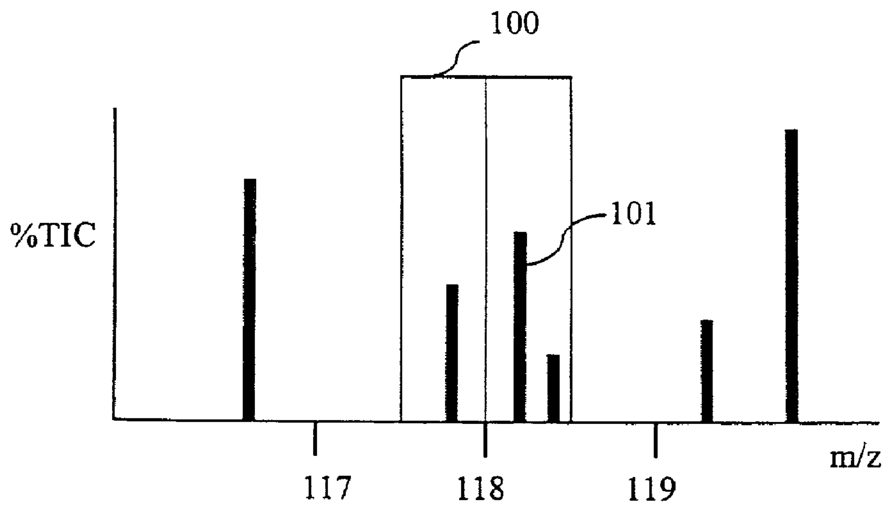
FIGS. 6A through 6D are graphs illustrating how the spectra are matched to the spectral characteristics in the present invention.

FIG. 6A shows a specified m/z of 118 with a window 100 centered at the specified m/z. The most abundant ion 101 within the window, shown as the highest peak indicating the ion's % TIC value, is identified. The score of the specified product ion with an m/z of 118 is the % TIC value of the ion 101.

The loss ion (neutral or charged) spectral characteristic is specified as a desired loss m/z value from the precursor. To match spectra to the specified loss ion characteristic for neutral losses, the ion loss m/z is calculated as the precursor m/z minus the specified loss m/z value. Then searching is performed in a window centered around the calculated ion loss m/z value ±c m/z and a most abundant ion $i_1$ in the window is selected. In this embodiment, c is set to 0.5. The product ion match of these spectra is then scored as the % TIC value $I_1$ for the selected ion as follows:

$$\text{Score}=I_1 \quad (2)$$

To match spectra to the specified loss ion characteristic for charged losses, the loss ion m/z is calculated by subtracting the specified loss m/z value from the predicted singly charged m/z value for the precursor instead of the actual precursor m/z (i.e., 2×precursor m/z−1).

Similar to the neutral loss case, a window centered around the calculated ion loss m/z value ±c m/z is then searched and a most abundant ion in the window is selected. In this embodiment, c is set to 0.5. The product ion match of these spectra is then scored as the % TIC value $I_1$ for the selected ion as follows:

$$\text{Score}=I_1 \quad (3)$$

Neutral losses result in product ions that have the same charge as the precursor ion. Thus, the m/z value used to calculate the ion loss m/z for a neutral loss from a doubly charged precursor is half that of the same mass loss from a singly charged precursor. In contrast, charged losses generate product ions that have a charge one unit less than that of a precursor and are only observed in spectra arising from doubly charged precursors. Accordingly, when a particular loss is entered as a search criterion, the precursor charge and the charge of the product ion produced by the loss are included in the loss description, allowing the user to define the loss as neutral or charged and to adjust the magnitude of a neutral loss to account for the precursor charge state.

Figure 6B:
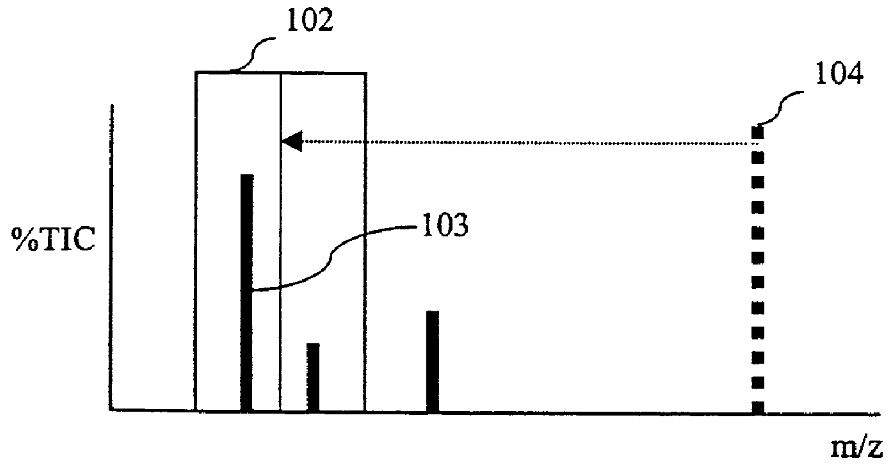

FIG. 6B shows a precursor m/z or estimated singly charged m/z value 104 and a window 102 which is a distance from the m/z value 104. This distance is the calculated loss m/z as described above. The most abundant ion 103 within the window 102, shown as the highest peak indicating the ion's % TIC value, is identified. The score of the specified ion loss is the % TIC value of the ion 103.

The ion pair spectral characteristic is specified as a distance (measured in units of m/z) between two fragment ions. This distance may reflect the residual mass of one or more amino acids or the elimination of specific adducts, adduct fragment, or other structural moiety. To match spectra to the specified ion pair spectral characteristic, a hypothetical list of fragment ions shifted the specified distance of m/z units above the actual fragment ions (i.e., the "real" list) in the spectra is first generated, then fragment m/z values in both lists are rounded to the nearest integer. Two windows centered at the respective rounded fragment m/z values ±d m/z are searched and most abundant ions $i_1, i_2$ in respective windows are selected. In this embodiment, d is set to 0.5. The ion pair match is then scored as the geometric mean of the % TIC values $I_1, I_2$ for the selected fragment ions from each of the rounded windows.

$$\text{Score}=(I_1 \cdot I_2)^{1/2} \quad (4)$$

Figure 6C:
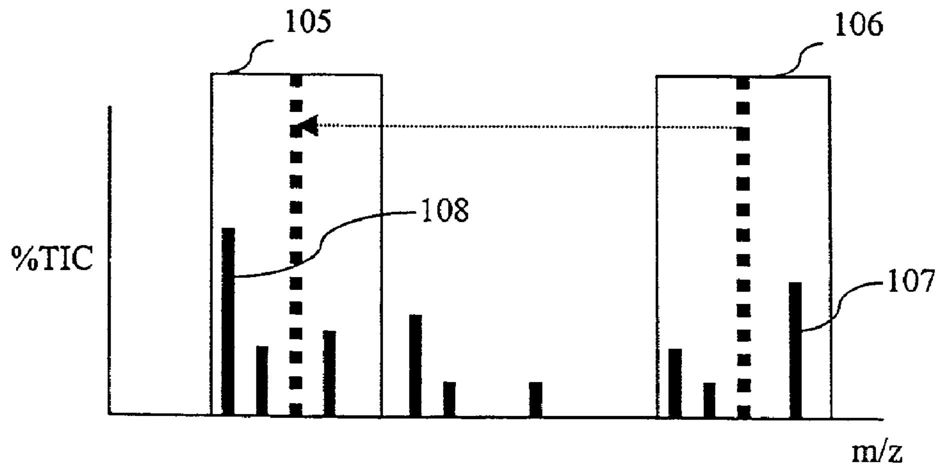

FIG. 6C shows rounded m/z ion pairs separated by a distance specified by the user. Windows 105 and 106 are centered around the ion pairs. The most abundant ions 107 and 108 within the respective windows 106 and 105, shown as the highest peaks indicating the ions' % TIC value, are identified. The score of the specified ion pair is the geometric mean of the respective % TIC values.

Figure 6D:
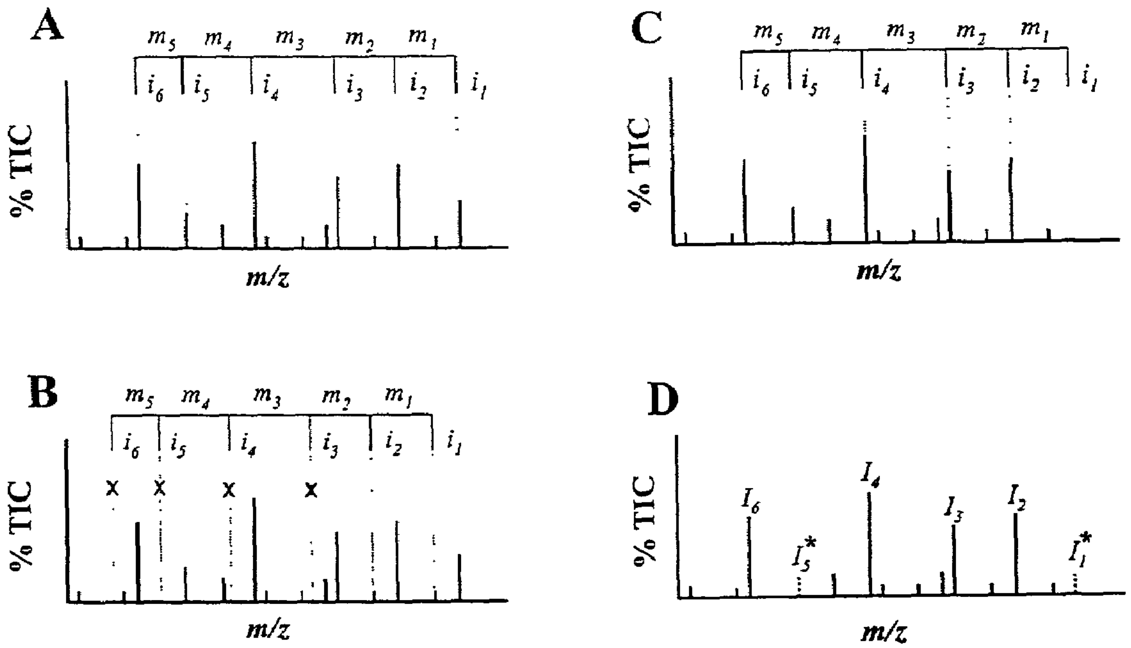

The ion series spectral characteristic is an extended form of the ion pair spectral characteristic in which multiple ions at multiple distances are matched. The ion series spectral characteristic is specified as a series of ions spaced by desired m/z values. Ion series are defined as a group of ions ($i_1$, $i_2$, $i_3$ . . . $i_n$) separated by specific m/z values ($m_1$, $m_2$, $m_3$ . . . $m_n$), where $m_n=i_n-i_{n+1}$ as shown in FIG. 6D. It should be noted that lower subscripts in an ion series denote higher m/z values. In the case of peptide sequence motifs, the distances between ions in the series correspond to the average residue masses of the amino acids in their sequence in the peptide. To match spectra to the ion series spectral characteristic, a hypothetical list of fragment ions separated by the average residue mass differences for amino acid series is first generated. The first ion in this hypothetical series ($i_1$) is then aligned with the highest m/z fragment ion in the actual MS—MS spectrum being evaluated as shown in graph A of FIG. 6D. The actual ions that align with the hypothetical ions are then detected within a window centered around a user-specified mass tolerance (typically ±0.5 m/z unit).

The ions detected by alignment with the hypothetical ion series are scored as described below. The hypothetical ion series is then aligned beginning with the next lower m/z ion in the MS—MS spectrum and the matches again are recorded and scored (FIG. 6D, graph B). A minimum number of ions x to be detected in order for the series to be scored may be specified. In the example depicted in graph B, only two matches are detected, $i_1$, $i_2$, and the spectrum would not be scored if x>2. The alignment and detection cycle is continued until the hypothetical ion series extends below the lower m/z limit of the spectrum, such that the user-specified minimum number of matches x cannot be detected. Because some MS—MS spectra may not contain all the ions in a particular series, the hypothetical series also is matched to the spectrum beginning with the second hypothetical ion ($i_2$) and matches between real ions and hypothetical ions $i_2$–$i_n$ then are recorded and scored (FIG. 6D, graph C). Alignments of the hypothetical ion series with MS—MS data are continued through ions $i_{n-x}$, where x is the user-specified minimum number of matches required for scoring.

Scoring of spectra is calculated from the % TIC values of the detected ions corresponding to hypothetical ions $i_1$–$i_n$ (FIG. 6D, graph D). The % TIC values corresponding to $i_1$, $i_2$, $i_3$ . . . $i_n$ are denoted $I_1$, $I_2$, $I_3$ . . . $I_n$, respectively. Scores for spectra are calculated as follows:

$$\text{Score}=N(I_1 \cdot I_2 \cdot I_3 \ldots \cdot I_n)^{1/n} \quad (5)$$

where N is the number of detected ions that correspond to hypothetical ions $i_1$–$i_n$ in the series. For spectra in which one or more of the ions in the series are missing, a value $I_n$ is inserted that is equal to a threshold value for ion detection, which may be set by the user (typically 0.2% TIC). In FIG. 6D, graph D, for example, the score is calculated as $$\text{Score}=4(I_1 \cdot I_2 \cdot I_3 \cdot I_4 \cdot I_5 \cdot I_6)^{1/6} \quad (6)$$

where only four of the six ions in the series (i.e., $I_2$, $I_3$, $I_4$, and $I_6$) were actually detected in the spectrum and threshold % TIC values are used for $I_1$ and $I_5$, which were not detected.

As noted above, if N<x (the user specified minimum number of detected ions), then a score of zero would be assigned to the spectrum.

To reduce background noise in scoring, each spectral characteristic is designated as either primary or secondary at the outset of the search. Secondary characteristics are then linked or paired with primary characteristics to permit identification of chemical species in which a desired structure occurs and to effectively detect unanticipated modifications in the mass spectral data. Examples of primary and secondary pairings include but are not limited to a product ion secondary to an ion series, a loss ion secondary to a product ion, multiple product ions secondary to a loss ion, and one ion series secondary to another ion series. Secondary spectral characteristics are entered in the same way as primary characteristics, except that secondary characteristics are each linked to a specific primary characteristic for the search. Whereas primary characteristics are automatically scored when detected, a secondary characteristic is only scored when the linked primary characteristic is detected in the same mass spectrum. Thus, the scoring of the secondary characteristic is contingent on the presence of other primary indicators. The primary and secondary characteristics are linked hierarchically. For example, spectral characteristics that are either weak or irregular indicators in spectra or that are common in background spectra are good candidates for secondary classification. Scores for secondary characteristics are adjusted to insure that the final scores are most heavily influenced by primary characteristics. The initial calculated % TIC score of a secondary characteristic is adjusted by taking the geometric mean of this score and the % TIC score of the primary characteristic on which it is linked. Each secondary characteristic is scored only once and is allowed a maximum score equal to the score of the linked primary characteristic. The final spectrum score is calculated as the sum of % TIC values of detected primary characteristics plus the sum of adjusted secondary characteristic scores. Each secondary ion category is scored only once per primary ion.

The scores are reported for all sets of averaged MS—MS scans receiving nonzero scores. In addition to the score, the scan number, retention time, the precursor m/z, and the ions detected in the MS—MS spectrum that matched the hypothetical series are reported. The scan number is the sequential identifier assigned by the data system to each MS or MS—MS scan in a datafile. The retention time is the elapsed time in the LC-MS-MS analysis when the MS or MS—MS scan was recorded. The precursor m/z is the m/z value of the precursor ion subjected to MS—MS. The ions detected are the m/z values of signals in the scored spectrum that matched search criteria. This makes it simple to identify spectra of interest. Finally, all of the primary and secondary ions or ion series, scored are reported alongside the spectrum identifiers. It is often possible to estimate spectrum quality directly from this information, prior to recovering the complete CID spectra for visual inspection.

It is to be understood that the primary and secondary characteristics of the present invention are not limited to hierarchical relationships, but may be linked in other ways, e.g. sequentially, in parallel, etc, depending on the chemical species analyzed.

Figure 6E:
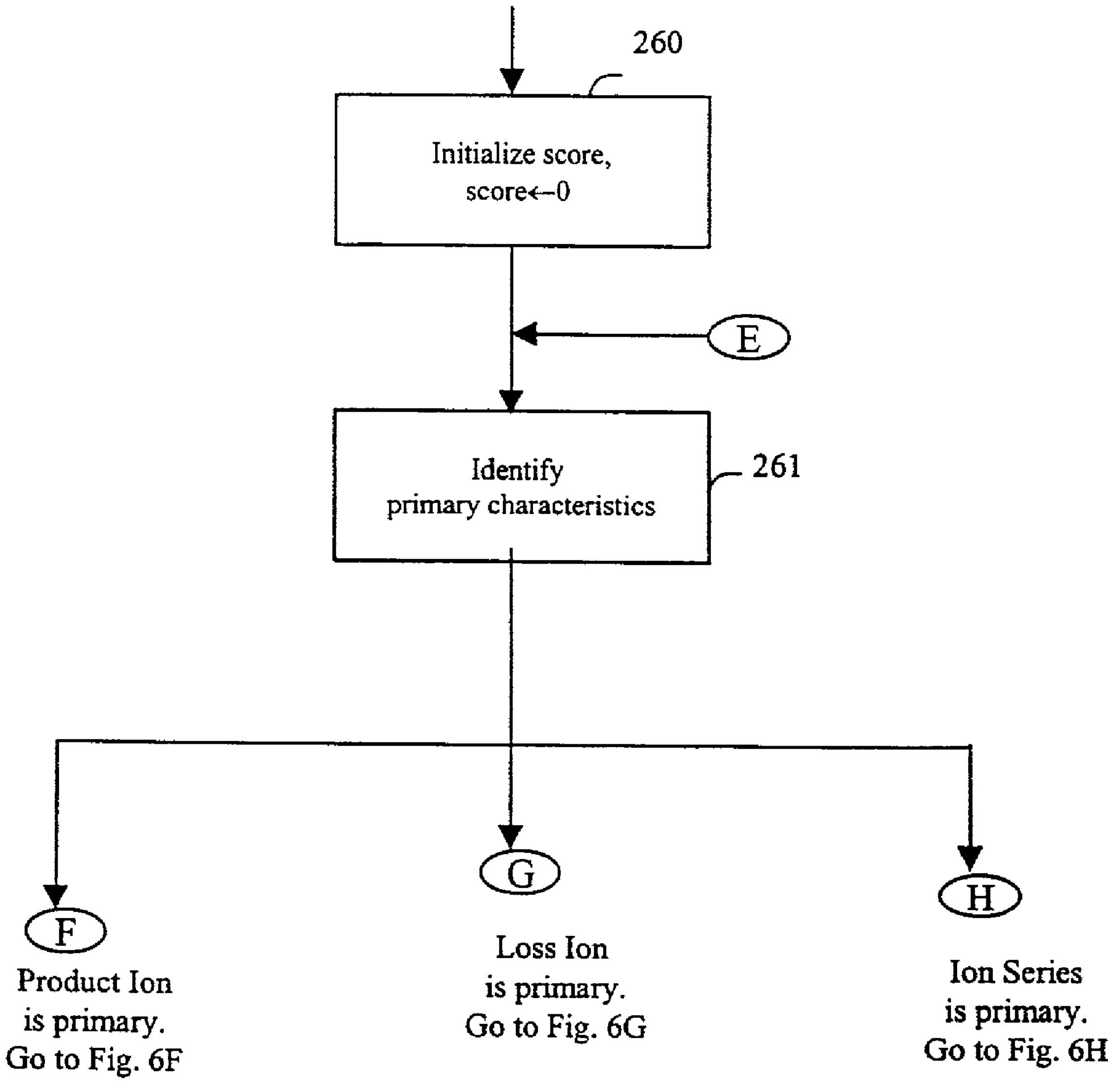
FIGS. 6E through 6I are flowcharts describing the scoring step of the embodiment of FIG. 4.
Figure 6F:
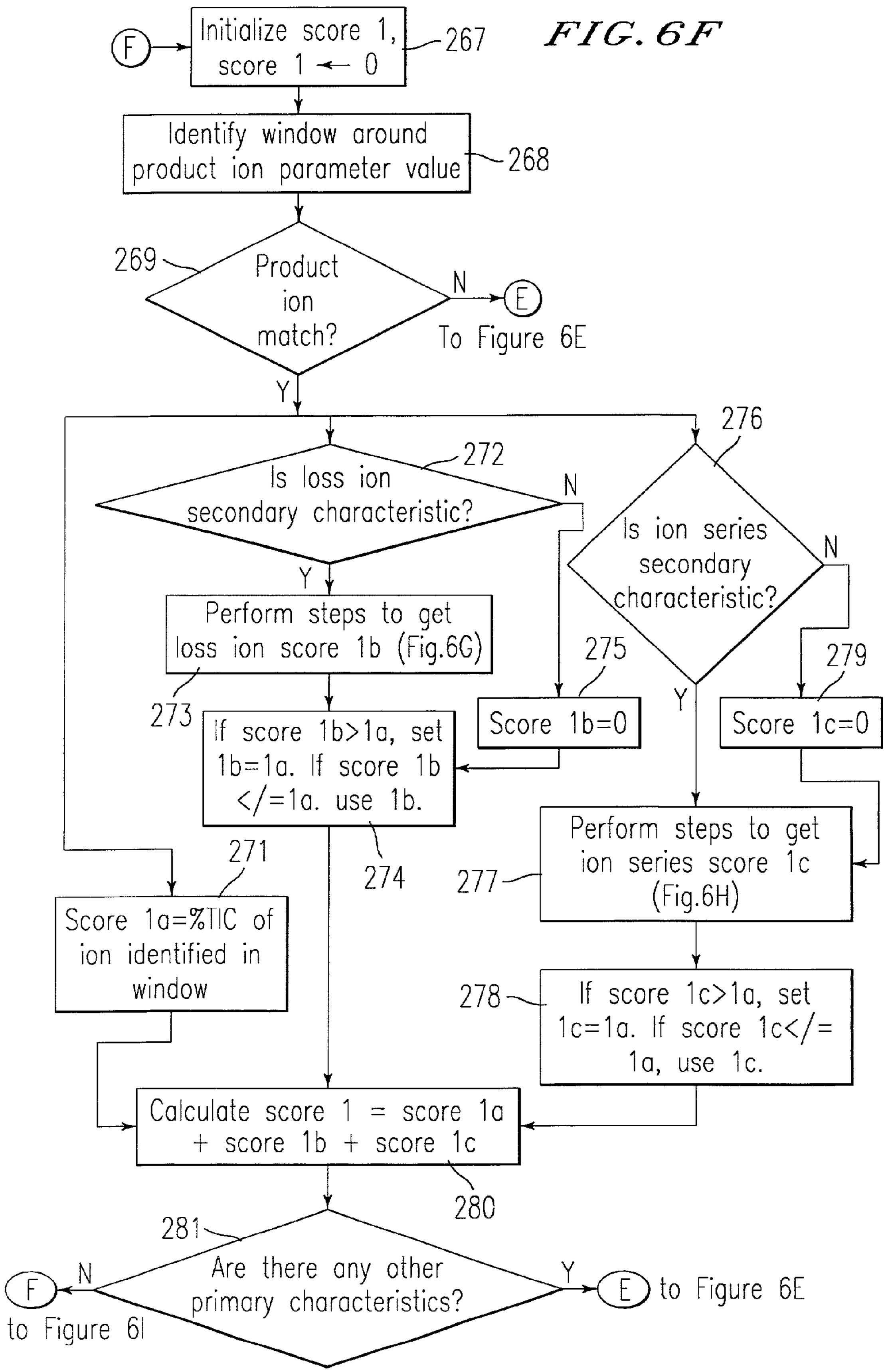
Figure 6G:
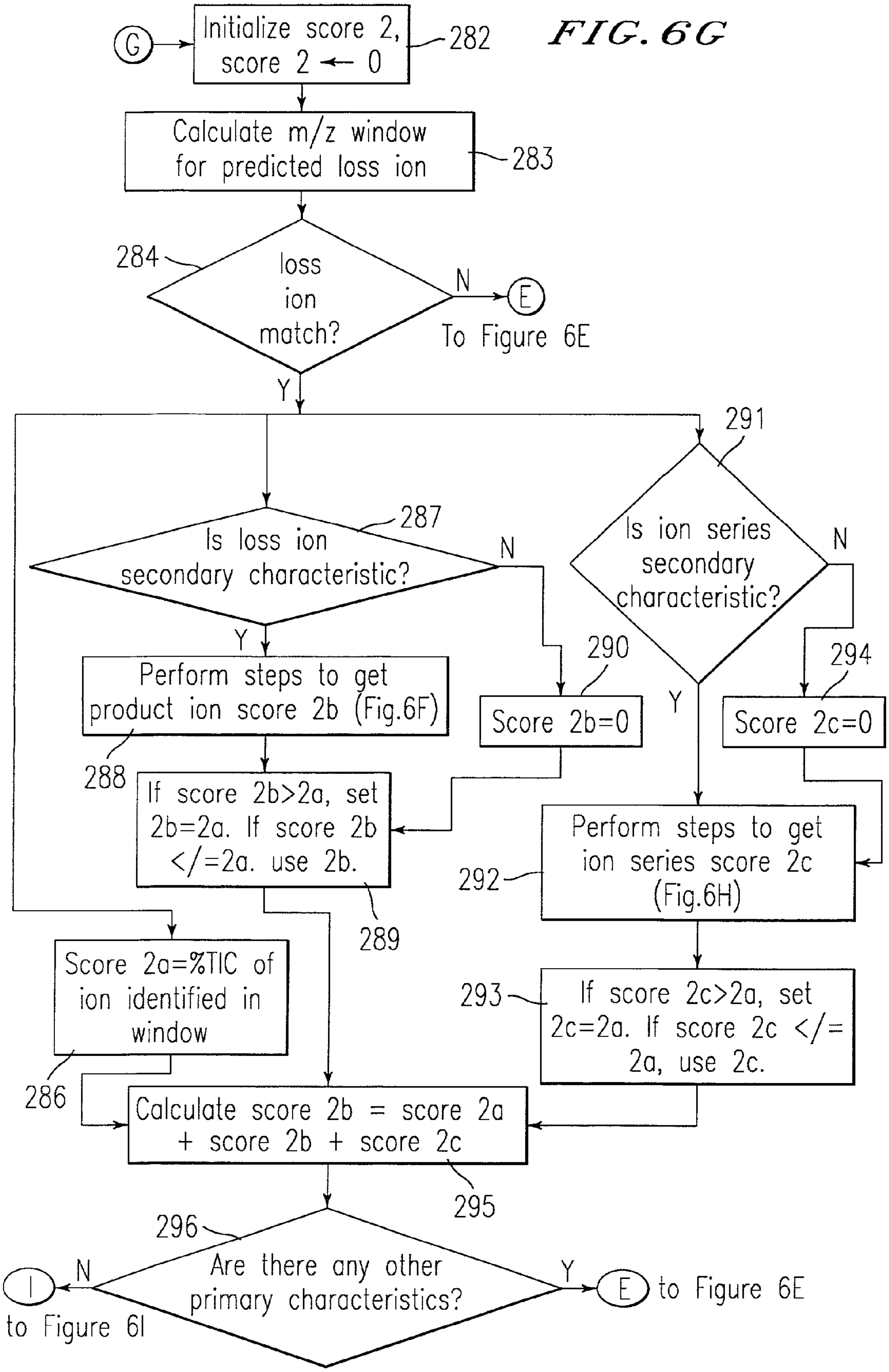
Figure 6H:
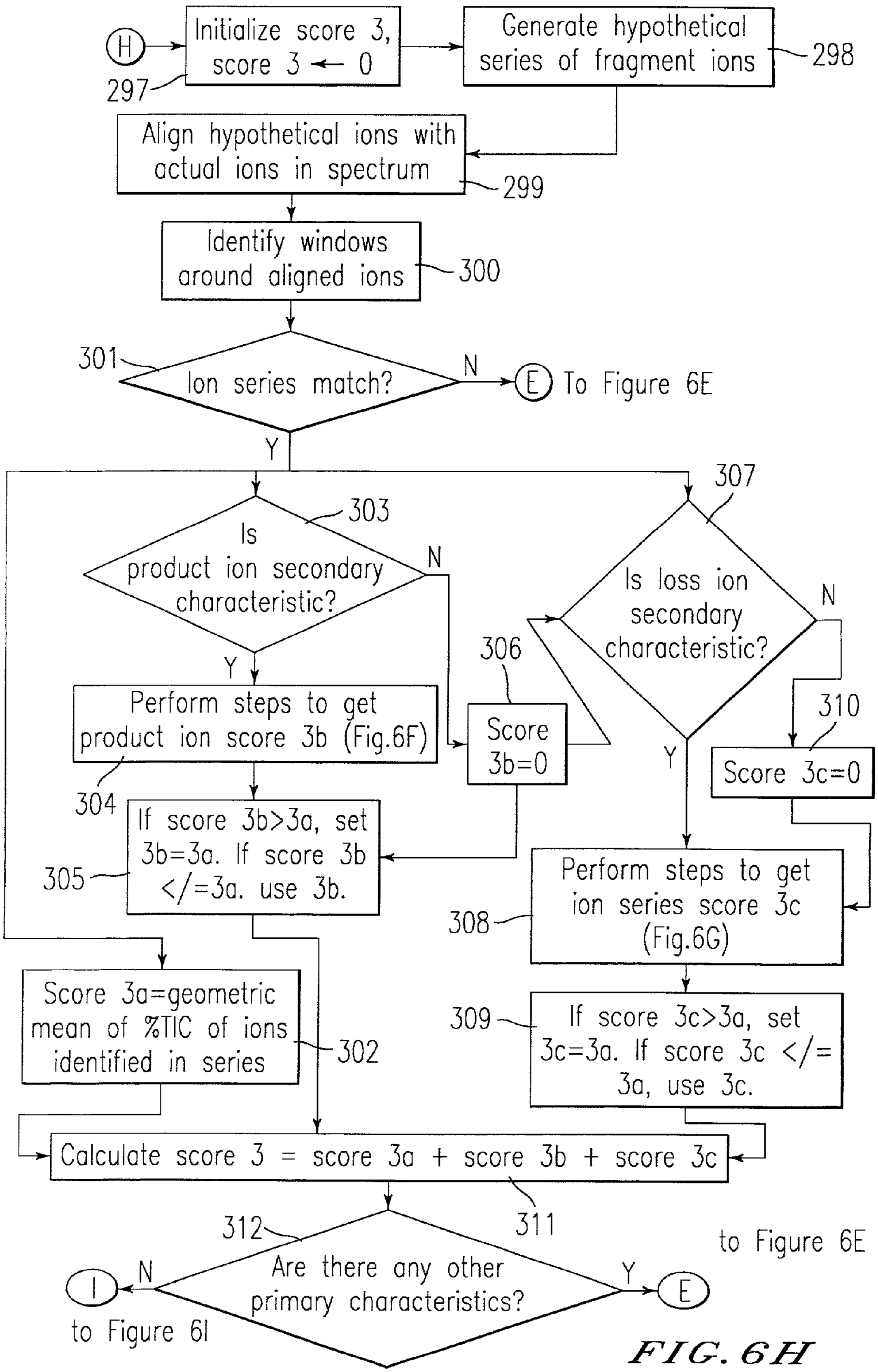

FIGS. 6E–6I show the steps for calculating the score based on the spectral characteristics specified. First, the score is initialized to zero in step 260. Then, the spectral characteristics designated by the user as primary are identified in step 261. If the product ion spectral characteristic (parameter) is designated as primary, then the steps for calculating the product ion score, score 1, as shown in FIG. 6F, are performed. If the loss ion parameter is designated as primary, then the steps for calculating the loss ion score, score 2, are performed as described in FIG. 6G. If the ion series parameter is designated as primary, then the steps for calculating the ion series score, score 3, as described in FIG. 6H, are performed. Otherwise, the score remains as zero and the process continues to the display step 210 of FIG. 4.

FIG. 6F shows the steps for calculating the product ion score, score 1, where the product ion is specified as a primary spectral characteristic. The product ion score, score 1, is initialized to zero in step 267. In step 268, a window centered at the specified product ion parameter m/z value ±0.5 m/z units is identified. In step 269, an inquiry is made as to whether a product ion match was found within the identified window. If the product ion match was not found, then the steps of FIG. 6E beginning with step 261 are performed to evaluate any other designated primary parameters. On the other hand, if the match was found, then in step 271, a product ion primary score, score 1$a$, is set to the % TIC value of the most abundant ion within the identified window.

Next, an inquiry is made in step 272 as to whether the loss ion spectral characteristic is secondary and linked to the primary product ion parameter. If so, the steps of FIG. 6G (to be discussed later) are performed to determine the loss ion secondary score, score 1$b$, in step 273. The secondary score does not exceed the primary score. According, in step 274, if score 1$b$ is greater than score 1$a$, then score 1$b$ is set equal to score 1$a$. Otherwise, score 1$b$ as calculated in step 273 is used. In step 272, if the loss ion is not the secondary search characteristic linked to the primary product ion parameter, then score 1$b$ is set to zero in step 275.

Next, an inquiry is made in step 276 as to whether the ion series spectral characteristic is secondary and linked to the primary product ion parameter. If so, the steps of FIG. 6H (to be discussed later) are performed to determine the ion series secondary score, score 1$c$, in step 277. As mentioned previously, secondary score does not exceed the primary score. Thus, in step 278, if score 1$c$ is greater than score 1$a$, then score 1$c$ is set equal to score 1$a$. Otherwise, score 1$c$ as calculated in step 277 is used. In step 279, if the ion series is not the secondary search characteristic linked to the primary product ion parameter, then score 1$c$ is set to zero in step 279.

The product ion score, score 1, is then calculated as the sum of score 1$a$, score 1$b$, and score 1$c$ in step 280. An inquiry is then made in step 281 as to whether other primary characteristics have been designated. If so, then the steps of FIG. 6E are performed to calculate the scores of the other designated primary characteristics. If there are not any other primary characteristics designated, score 1 is then used in the steps of FIG. 6I (to be discussed later) to calculate the total mass spectral score.

It is to be understood that multiple product ions with different m/z values may be designated as primary characteristics. In this case, the product ion score, score 1, is the sum of the product ion score for each product ion.

FIG. 6G shows the steps for calculating the loss ion score, score 2, where the loss ion is specified as a primary spectral characteristic. Beginning with step 282, the loss ion score, score 2, is initialized to zero. In step 283, a window centered at a calculated loss ion m/z value ±0.5 m/z units is identified. If the loss is a neutral loss, then the loss ion m/z is calculated as the precursor m/z minus the specified loss ion parameter m/z value. If the loss is a charged loss, then the loss ion m/z is calculated by subtracting the specified m/z from the predicted singly charged m/z value for the precursor (i.e., 2×precursor m/z−1). In step 284, an inquiry is made as to whether a loss ion match was found within the identified window. If the loss ion match was not found, then the steps of FIG. 6E beginning with step 261 are performed to evaluate any other designated primary parameters. On the other hand, if the match was found, then in step 286, a loss ion primary score, score 2*a*, is set to the % TIC value of the most abundant ion within the identified window.

Next, an inquiry is made in step 287 as to whether the product ion spectral characteristic is secondary and linked to the primary loss ion parameter. If so, the steps of FIG. 6F are performed to determine the product ion secondary score, score 2*b*, in step 288. The secondary score does not exceed the primary score. According, in step 289, if score 2*b* is greater than score 2*a*, then score 2*b* is set equal to score 2*a*. Otherwise, score 2*b* as calculated in step 288 is used. In step 272, if the product ion is not the secondary search characteristic linked to the primary loss ion parameter, then score 2*b* is set to zero in step 290.

Next, an inquiry is made in step 291 as to whether the ion series spectral characteristic is secondary and linked to the primary loss ion parameter. If so, the steps of FIG. 6H (to be discussed later) are performed to determine the ion series secondary score, score 2*c*, in step 292. The secondary score does not exceed the primary score. Thus, in step 293, if score 2*c* is greater than score 2*a*, then score 2*c* is set equal to score 2*a*. Otherwise, score 2*c* as calculated in step 292 is used. In step 294, if the ion series is not the secondary search characteristic linked to the primary loss ion parameter, then score 2*c* is set to zero in step 294.

The loss ion score, score 2, is then calculated as the sum of score 2*a*, score 2*b*, and score 2*c* in step 295. An inquiry is then made in step 296 as to whether other primary characteristics have been designated. If so, then the steps of FIG. 6E are performed to calculate the scores of the other designated primary characteristics. If there are not any other primary characteristics designated, score 2 is then used in the steps of FIG. 6I (to be discussed later) to calculate the total mass spectral score.

It is to be understood that multiple loss ions may be designated as primary characteristics. In this case, the loss ion score, score 2, is the sum of the loss ion score for each loss ion.

FIG. 6H shows the steps for calculating the ion series score, score 3, where the ion series is specified as a primary spectral characteristic. In step 297, the ion series score, score 3, is initialized to zero. In step 298, a hypothetical list of fragment ions separated by the average residue mass differences of amino acid series is first generated. In step 299, the first ion in this hypothetical series is then aligned with the highest m/z fragment ion in the actual MS—MS spectrum being evaluated. In step 300, windows are identified which are centered around a user-specified m/z tolerance (typically ±0.5 m/z units) corresponding to the actual ions that align with the hypothetical ions. In step 301, an inquiry is made as to whether an ion series match was found within the identified windows. If the ion series match was not found, then the steps of FIG. 6E beginning with step 261 are performed to evaluate any other designated primary parameters. On the other hand, if the match was found, then in step 302, an ion series primary score, score 3*a*, is set as the geometric mean of the % TIC values of the most abundant ions within the respective windows. It should be noted that a score for ion pair characteristics can be calculated using the ion series steps of FIG. 6H, where the number of windows (and ions) identified and used in score 3*a* is two.

Next, an inquiry is made in step 303 as to whether the product ion spectral characteristic is secondary and linked to the primary ion series parameter. If so, the steps of FIG. 6F are performed to determine the product ion secondary score, score 3*b*, in step 304. The secondary score does not exceed the primary score. According, in step 305, if score 3*b* is greater than score 3*a*, then score 3*b* is set equal to score 3*a*. Otherwise, score 3*b* as calculated in step 304 is used. In step 305, if the product ion is not the secondary search characteristic linked to the primary loss ion parameter, then score 3*b* is set to zero in step 306.

Next, an inquiry is made in step 307 as to whether the loss ion spectral characteristic is secondary and linked to the primary ion series parameter. If so, the steps of FIG. 6G are performed to determine the loss ion secondary score, score 3*c*, in step 308. The secondary score does not exceed the primary score. Thus, in step 309, if score 3*c* is greater than score 3*a*, then score 3*c* is set equal to score 3*a*. Otherwise, score 3*c* as calculated in step 308 is used. In step 310, if the loss ion is not the secondary search characteristic linked to the primary ion series parameter, then score 3*c* is set to zero in step 310.

The ion series score, score 3, is then calculated as the sum of score 3*a*, score 3*b*, and score 3*c* in step 311. An inquiry is then made in step 312 as to whether other primary characteristics have been designated. If so, then the steps of FIG. 6E are performed to calculate the scores of the other designated primary characteristics. If there are not any other primary characteristics designated, score 3 is then used in the steps of FIG. 6I (to be discussed later) to calculate the total mass spectral score.

It is to be understood that multiple ion series may be designated as primary characteristics. In this case, the ion series score, score 3, is the sum of the ion series score for each ion series.

Figure 6I:
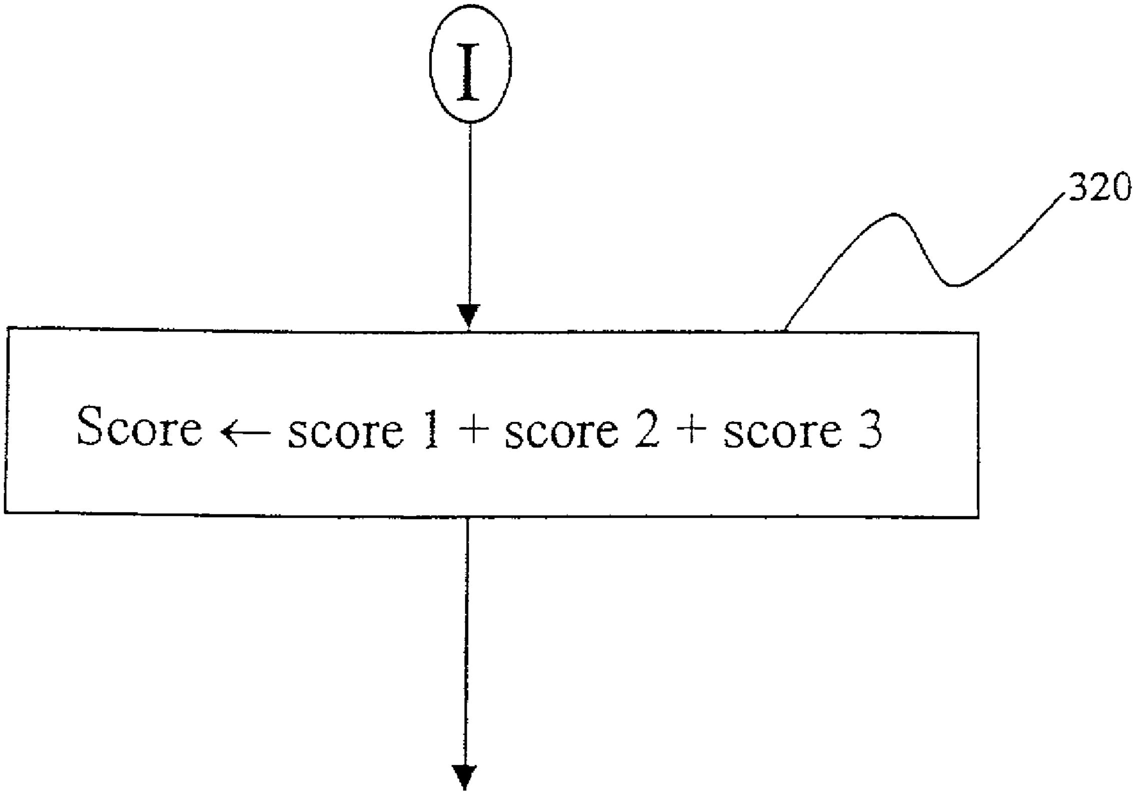

FIG. 6I shows the step for calculating the total score of the mass spectral data being analyzed. In step 320, the total score, score, is calculated as the sum of score 1, calculated as in FIG. 6F, score 2, calculated as in FIG. 6G, and score 3, calculated as in FIG. 6H. The score is then displayed as shown in step 210 of FIG. 4, for example. It is to be understood that additional spectral characteristics can be added and scored.

Figure 7A:
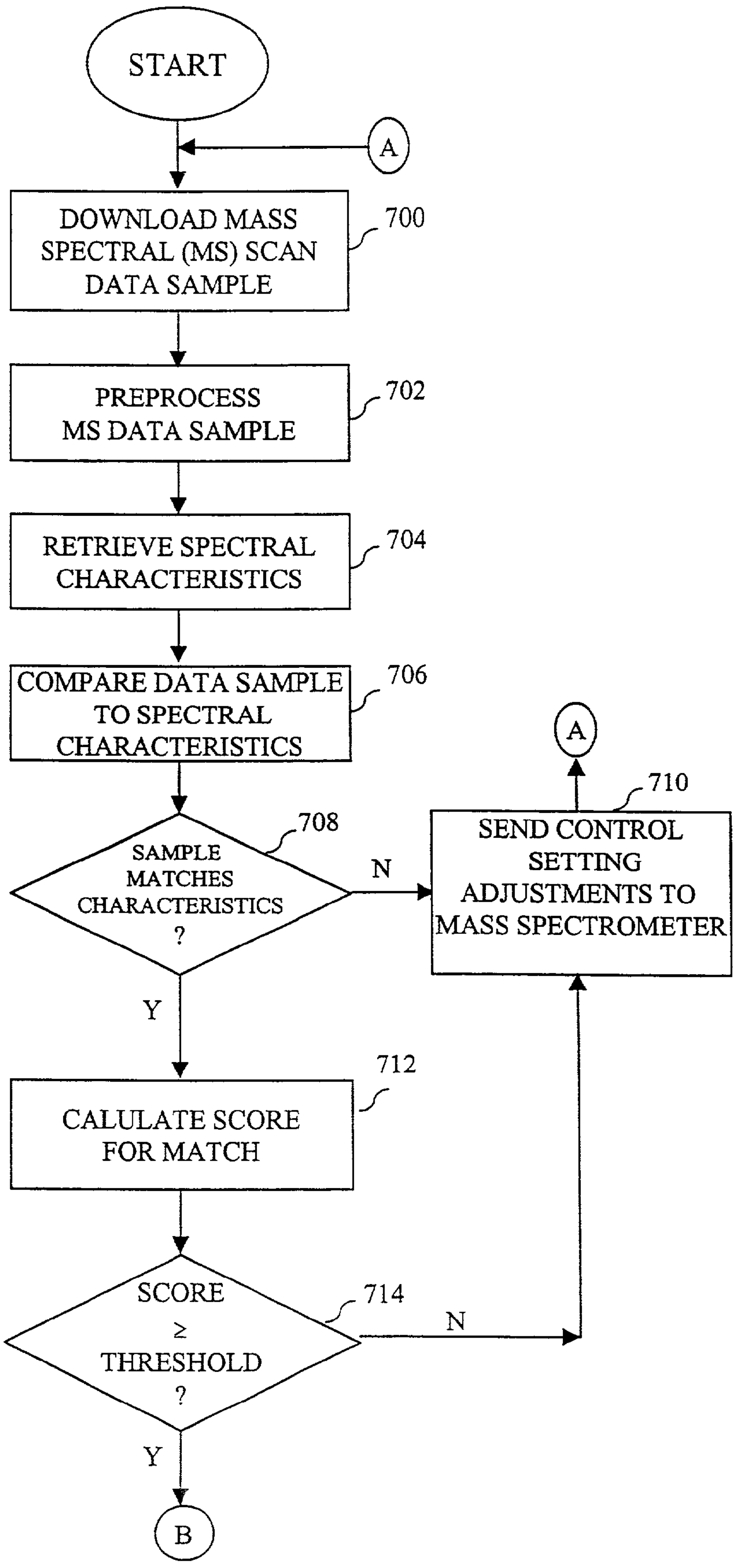
FIGS. 7A and 7B are flowcharts of another embodiment describing a method for mining mass spectral data real-time and adjusting the control settings of the mass spectrometer based on the results of the mining operation according to the present invention.
Figure 7B:
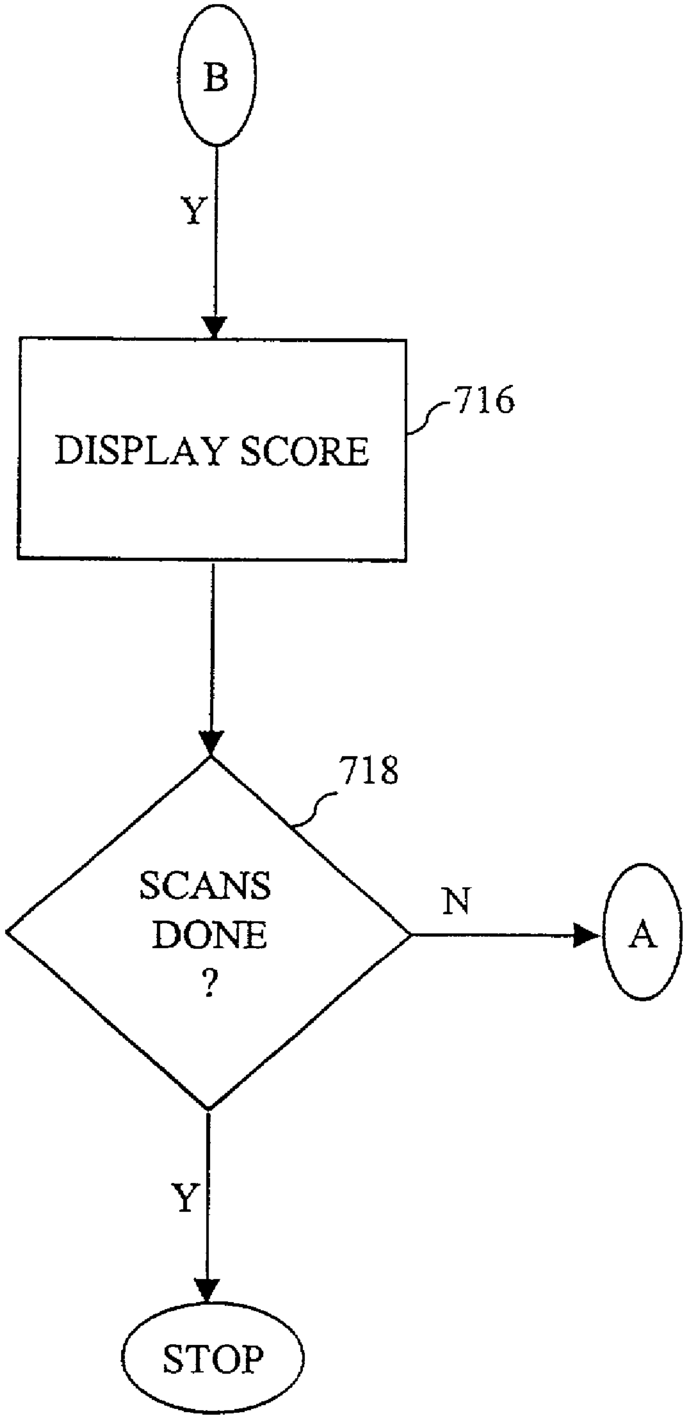

FIGS. 7A and 7B show another embodiment of a method for mining mass spectral data of the present invention. In this embodiment, the mass spectral mining is performed in real time so that the control settings of the mass spectrometer can be adjusted to improve the generated spectra. Exemplary control settings may include, but are not limited to, source energy, collision energy, resolution for precursor ion selection, and detector gain settings. So, in step 700 of FIG. 7A, a first sample is scanned and its spectral data downloaded to the host computer 20. In step 702, the data is preprocessed according to the steps in FIG. 5. The preprocessing step eliminates bias toward detection of more highly abundant species and permits identification of species present at low concentrations. Prior to analysis, the user has entered the spectral characteristics and their relationships upon which to search and score the data in step 704. This step allows the user to specify the spectral characteristics and relationships that are most useful in identifying a given chemical species and in effectively detecting unanticipated modifications in data. The data is compared to the spectral characteristics in step 706. An inquiry is made as to whether the data matches the spectral characteristics in step 708. If not, then in step 710, control setting adjustments are sent to the mass spectrometer and the process repeats beginning with step 700.

If, however, in step 708, the data matches the spectral characteristics, then a score is calculated in step 712 according to the steps in FIGS. 6E–61. In step 714, an inquiry is made as to whether the calculated score exceeds a predetermined threshold. If not, then the control setting adjustments are sent to the mass spectrometer in step 710 and the process repeats beginning with step 700.

If, however, the score exceeds the predetermined threshold, then a match is made and the result is displayed in step 716 in easily comprehensible tabular or graphical form as shown in FIG. 7B. If all the scans for the data sample are not completed, in step 718, then the process repeats for the next scan beginning with step 700. Otherwise, the process ends.

Figure 8:
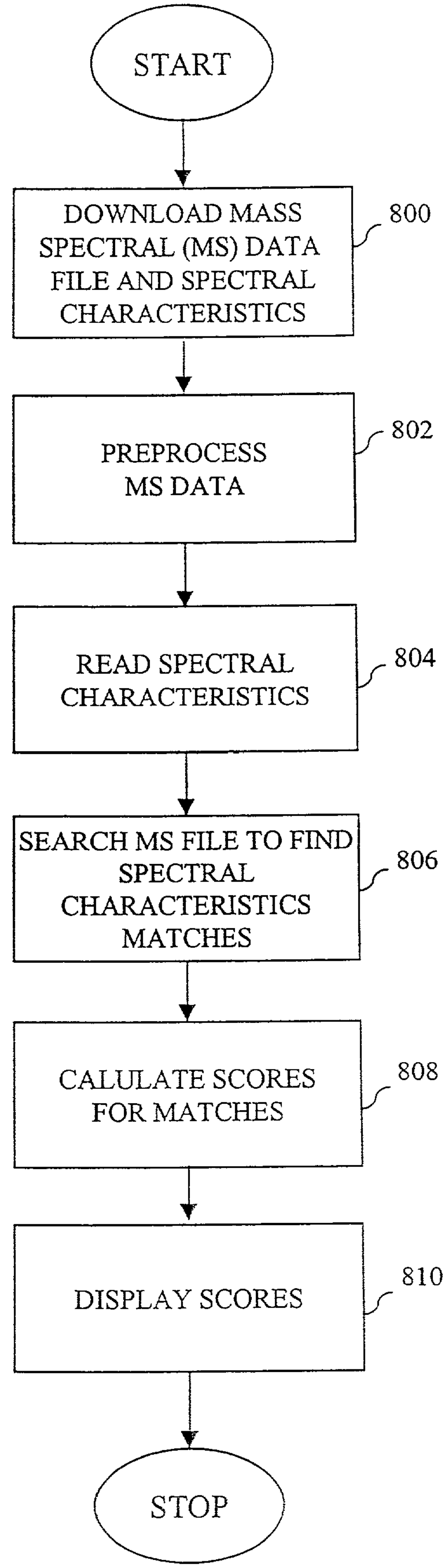
FIG. 8 is a flowchart of still another embodiment describing a method for mining mass spectral data in which the spectral characteristics are predetermined based on the data and input automatically.

FIG. 8 is yet another embodiment of a method for mining mass spectral data of the present invention in which the spectral characteristics and their relationships are automatically specified based on predetermined characteristics of the chemical species being analyzed. Accordingly, in step 800, the mass spectral data file and the spectral characteristics and their relationships associated with the analyzed chemical species are downloaded to the host computer 20. The spectral characteristics and their relationships may be stored in a data file, for example. Then the data is preprocessed in step 802 according to the steps in FIG. 5. The preprocessing step eliminates bias toward detection of more highly abundant species and permits identification of species present at low concentrations. Then the spectral characteristics and their relationships are read in step 804. The specified spectral characteristics and relationships are predetermined to be most useful in identifying a given chemical species and in effectively detecting unanticipated modifications in data. It is to be understood that the user can update the automatically specified characteristics after they are loaded. In step 806, the data file is searched for spectra corresponding to the spectral characteristics. Scores are calculated for the matches in step 808 as described in FIGS. 6E–6I. Then, in step 810, the results are displayed for the user in tabular or graphical form.

It is to be understood that the methods for mining a mass spectral data of FIGS. 4–8 may be performed over the Internet 35 instead of over the LAN 25 such that the computers are remote from each other. Or, the instrument computer 10 may perform the data mining functions such that the host computer 20 is not used.

Figure 9:
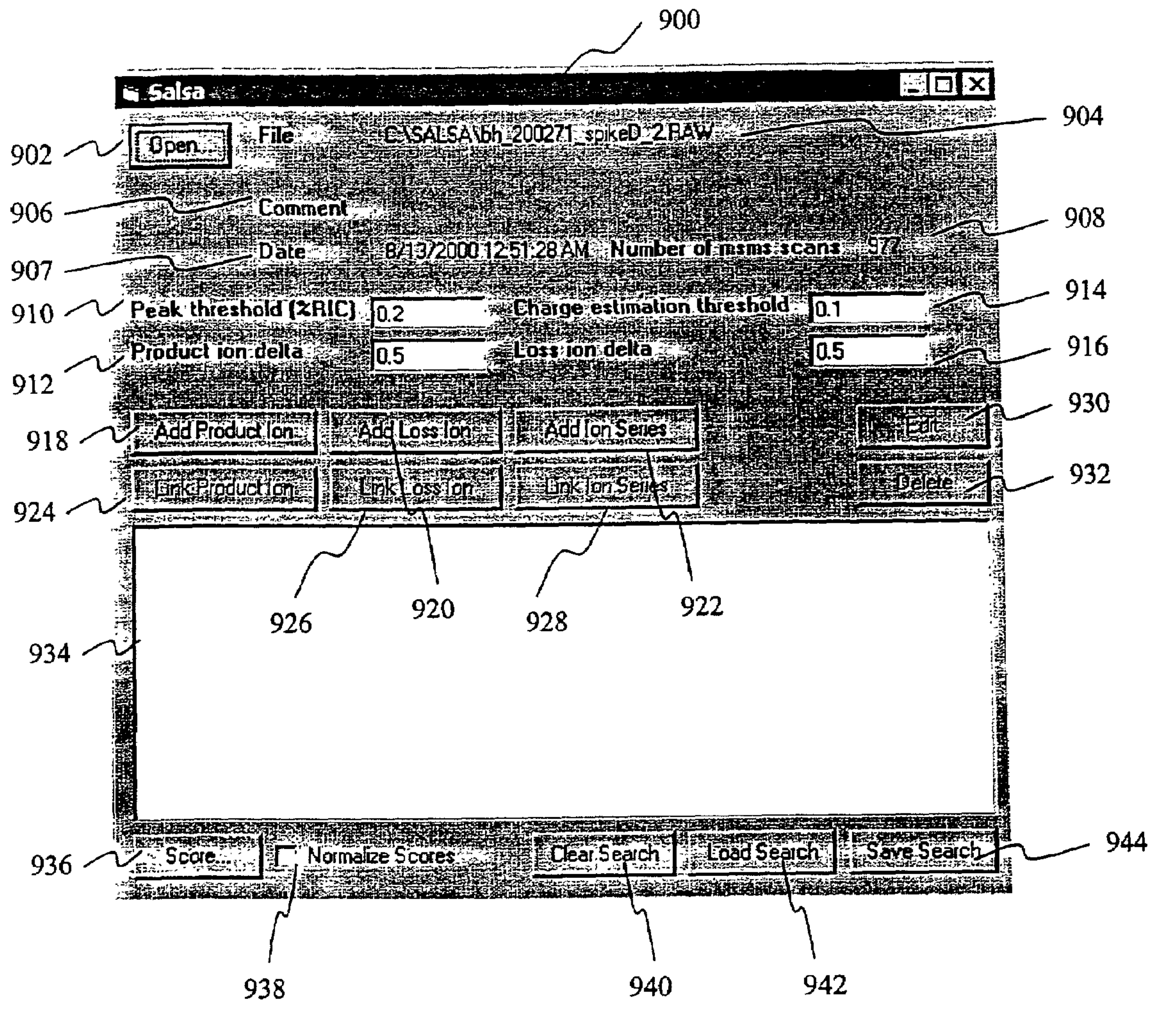
FIG. 9 shows a control window, which is part of a graphical user interface, used to input spectral characteristics for mining mass spectral data.

FIG. 9 shows an exemplary control window 900 by which the user inputs spectral characteristics of the mass spectral data used for a database or a data file to identify and extract the data of interest. Exemplary spectral characteristics include product ions at specific m/z values, neutral or charged losses from singly- or doubly-charged precursors, and ion series or pairs. Through this window 900, the user selects the file containing the data to be mined by clicking the Open button 902. Upon clicking the Open button 902, a list of all the mass spectral data files appears, allowing the user to browse for the data file to be analyzed. The user clicks on the desired data file and the system opens the file and returns the user to the control window 900. Once the file is opened, the file path appears in field 904, any comment or notes associated with the data file appear in field 906, the date and time that the data file was created appear in field 907, and the number of sets of averaged MS—MS scans stored in the data file appears in field 908.

The user inputs parameters in fields 910, 912, 914, and 916 used for preprocessing the mass spectral data. In field 910, the user inputs the peak threshold (% TIC). The peak threshold is the minimum % TIC value that the data must exceed in order to be considered in a search. The minimum value is determined by the intensity of an ion peak divided by the ion's total ion current, indicating the strength of the mass spectral data and whether the data is spurious or real. An exemplary peak threshold is 0.2%. In field 912, the user inputs the product ion delta value. The product ion delta refers to a mass window centered at the user-specified product ion m/z value, which has the width of +/− the entered product ion delta value. An exemplary product ion delta is 0.5. Ions will only be selected from the mass spectral data as product ions if they fall within this defined window. The user inputs the charge estimate threshold in field 914. For neutral and charged loss ion calculations, whether the precursor ion is singly- or doubly-charged is determined. To make this determination, the percentage of the total ion current above the precursor m/z is reviewed. If the percentage is less than or equal to the charge estimate threshold, the MS—MS scan is assigned as coming from a singly charged precursor ion. If the percentage is greater than the charge estimate threshold, the precursor ion is assigned as doubly-charged. An exemplary charge estimation threshold ranges between 0.1 and 0.15. The user enters the loss ion delta in field 916. The loss ion delta refers to a mass window centered at the designated loss ion m/z value, which has the width of +/− the entered loss ion delta value. Ions will only be selected as loss ions if they fall within this window. An exemplary loss ion delta is 0.5.

The user then defines the spectral characteristics used to mine the mass spectral data. In this case, the spectral characteristics specified are product ion, loss (neutral or charged) ion, and ion series (or pairs). If the user wants to mine for mass spectral data in which a specific product ion occurs, then the user selects the Add Product Ion button 918. If the user wants to mine for spectral data in which a charge loss from a precursor ion occurs during MS—MS fragmentation, then the user clicks on the Add Loss Ion button 920. Or if the user wants to mine for mass spectral data in which a series of ions occurs, then the user clicks on the Add Ion Series button 922. Upon clicking on each of these buttons 918, 920, and 922, respective parameter windows appear in which the user specifies the spectral characteristic values for which the search is conducted. The parameter windows will be explained below.

If the user wants the spectral characteristic to be a secondary spectral characteristic, the user first highlights the primary spectral characteristic which is displayed in the window 934 after being specified. Then, if the user want the product ion characteristic to be secondary in the search, then the user clicks on the Link Product Ion button 924. The product ion parameter window then opens and the user inputs the product ion spectral characteristics desired. Similar steps are performed when the loss ion characteristic is secondary by clicking the Link Loss Ion button 926 and when the ion series characteristic is secondary by clicking on the Link Ion Series button 928.

After the spectral characteristics and their relationships are defined, they are displayed in the window 934. The primary spectral characteristics are displayed first and the secondary spectral characteristics indented and underneath them.

If the user wants to edit spectral characteristics already specified, then the user highlights the characteristic in the window 934 and clicks on the Edit button 930. The corresponding parameter window appears and the user edits the data therein. The user may also delete spectral characteristics already specified by highlighting the characteristic in the window 934 and clicking on the Delete button 932. The characteristic is then deleted from the window 934 and from the search.

After the user has specified the spectral characteristics to be used to mine the mass spectral data, the user clicks the Score button 936 to perform the mining process and assign scores to the results to indicate how well the results correspond to the specified spectral characteristics. If the Normalized Scores box 938 has been checked prior to performing the mining process, then the scores displayed are the actual scores divided by the mean score of all the scores. The Clear Search button 940 allows the user to clear all the parameters from the control window 900 and start over. The Load Search button 942 allows the user to load parameters from a previous search. And the Save Search button 944 allows the user to save the currently displayed parameters.

FIGS. 10–13 show the parameter windows previously mentioned which appear upon clicking the spectral characteristic buttons 918, 920, and 922, allowing the user to input the spectral characteristic values used to mine the mass spectral data.

Figure 10:
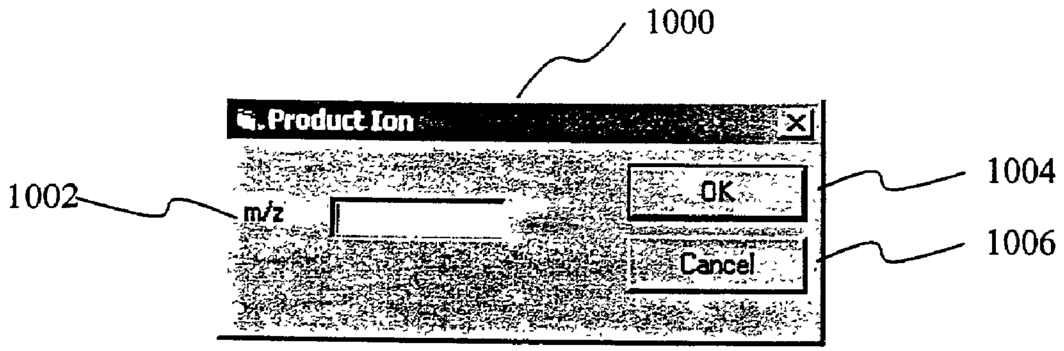
FIG. 10 shows a product ion parameter window, which is part of the graphical user interface, used to input product ion spectral characteristics for mining mass spectral data.

FIG. 10 shows an exemplary product ion parameter window 1000 which appears upon clicking the Add Product Ion button 918 in FIG. 9. The user-specified product ion m/z value is entered in field 1002. After the user enters the specified value, the user clicks the OK button 1004 if the value is correct. If the user decides not to input a value, then the user clicks the Cancel button 1006 to close the parameter window 1000.

Figure 11:
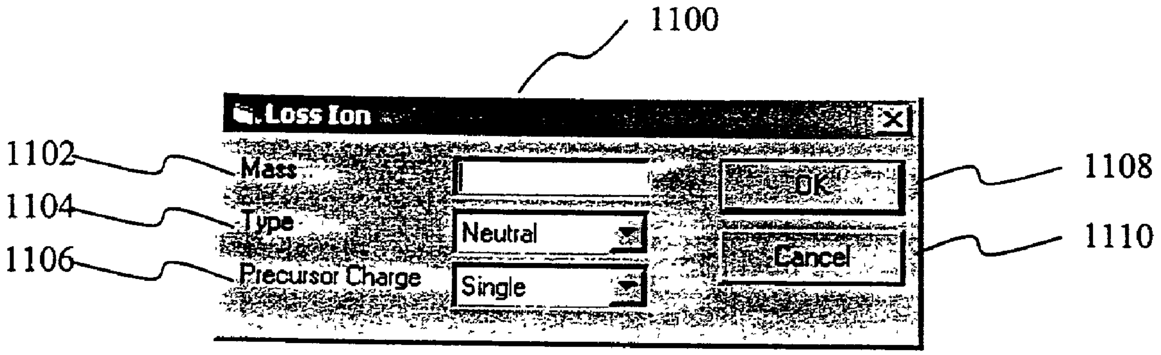
FIG. 11 shows a loss ion parameter window, which is part of the graphical user interface, used to input loss ion spectral characteristics for mining mass spectral data.

FIG. 11 shows an exemplary loss ion parameter window 1100 which appears upon clicking the Add Loss Ion button 920 in FIG. 9. The user can specify the mass of the loss ion in field 1102. The user can specify the type of loss ion in the pull-down window 1104 as a neutral ion or a charged ion. In the pull-down window 1106, the user can specify the precursor ion charge as single, double, or either. If "either" is specified, the fact that a neutral loss from a doubly-charged precursor ion appears to be half as much as loss of the same neutral ion from a singly-charged precursor ion is automatically accounted for in the score. The charge estimation threshold 914 in FIG. 9 is used to determine the precursor charge state and then the calculation of the precursor charge is adjusted accordingly. If parameters specified are correct, then the user clicks the OK button 1108. Otherwise, the user clicks the Cancel button 1110 to close the parameter window 1100 and start over.

Figure 12:
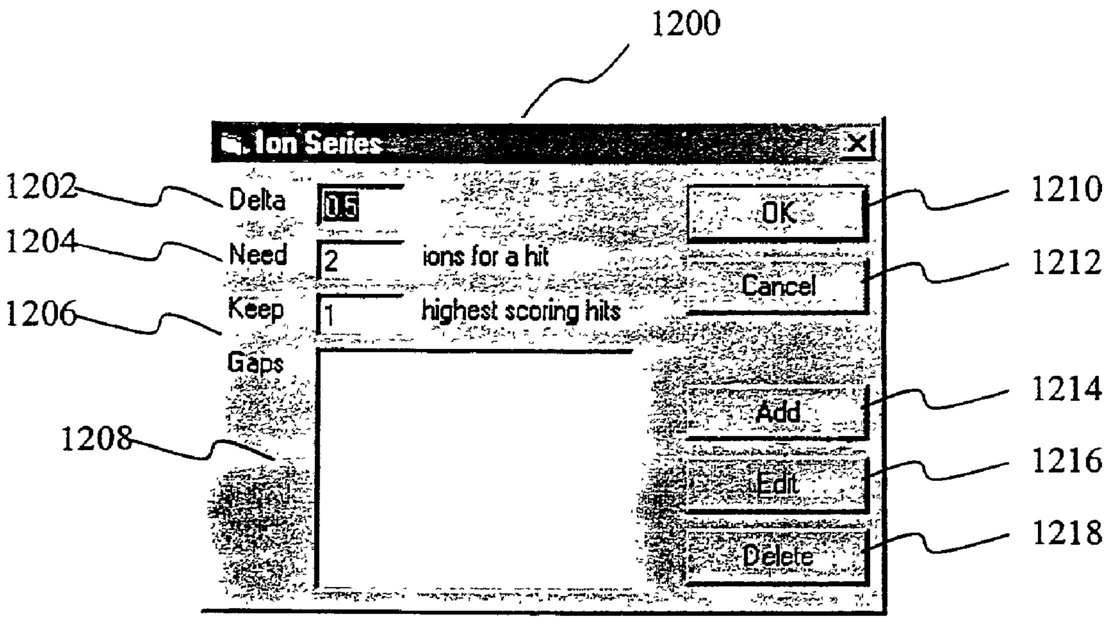
FIG. 12 shows an ion series parameter window, which is part of the graphical user interface, used to input ion series (or pair) spectral characteristics for mining mass spectral data.

FIG. 12 shows an exemplary ion series parameter window 1200 which appears upon clicking the Add Ion Series button 922 in FIG. 9. The user can specify a delta value in field 1202, which refers to a mass window centered at the designated m/z value which has the width of +/− the entered delta value. Ions will only be selected as part of an ion series if they fall within this window. An exemplary delta value is 0.5. The user then inputs the minimum number of ions in an MS—MS scan in field 704 that should match the specified ion series in order for the scan to be scored. An exemplary number is 2. At a minimum number of 2, most MS—MS scans generally receive a score, many of which are relatively low. A higher minimum number reduces the number of scans in the results, but may preclude detection of weaker, but real, results. In field 1206, the user inputs how many of the highest scoring matches to keep. The highest scores indicate the best alignments of the ions in the series with the user-specified ion series characteristics. An exemplary value is 1. Many scans may have more than one series of ions that match the user-specified series. The window 1208 is used to display the series to be mined. The user inputs the series by clicking the Add button 1214 at which a parameter window appears (to be discussed below). If the values entered are correct, then the user selects the OK button 1210. Otherwise, the user selects the Cancel button 1212 and starts over. If the user wants to edit the added information displayed in the window 1208, then the user highlights the information and clicks the Edit button 1216. The parameter window appears and the user edits the series previously specified. If the user wants to delete added information in the window 1208, then the user highlights the information and clicks the Delete button 1218. The information is deleted from the window 1208 and the search.

Figure 13:
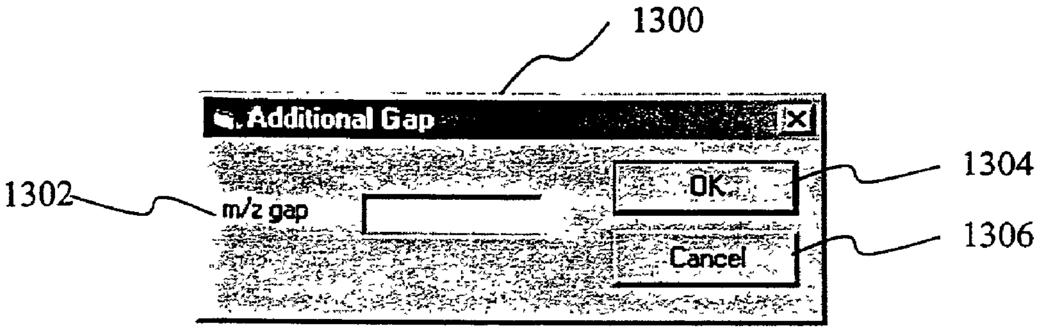
FIG. 13 shows an additional ion series gap parameter window, which is part of the graphical user interface, used to input additional ion series gap spectral characteristics for mining mass spectral data.

FIG. 13 shows an exemplary additional gap parameter window 1300 which appears upon clicking the Add button 1214 in FIG. 12 as previously mentioned. In this window, the term "gap" refers to the numerical spacing between ions on the m/z axis of the spectrum to be mined. In field 1302, capital letters or numerical values may be entered to represent the series or gaps to be mined. Capital letters representing an amino acid sequence of a peptide can be typed into this field 1302. A maximum of 14 amino acids can be used to search. When the sequence is entered correctly, the OK button 1304 is clicked. Otherwise, the user may click the Cancel button 1306 to close the parameter window 1300. Numerical values for m/z gaps are entered one at a time. The first numerical value is entered in the additional gap dialogue box 1300 and the OK button 1304 is clicked. To enter the next numerical value, the Add button 1214 in FIG. 12 is again selected and another numerical value is entered in field 201. 1302 of FIG. 13. When the amino acids are entered in an N to C terminal direction, then searching is performed to find the ions that correspond to the y-ions. To search for the b-ions in the amino acid sequence, the sequence can be entered backwards in the C to N terminal direction.

Figure 14:
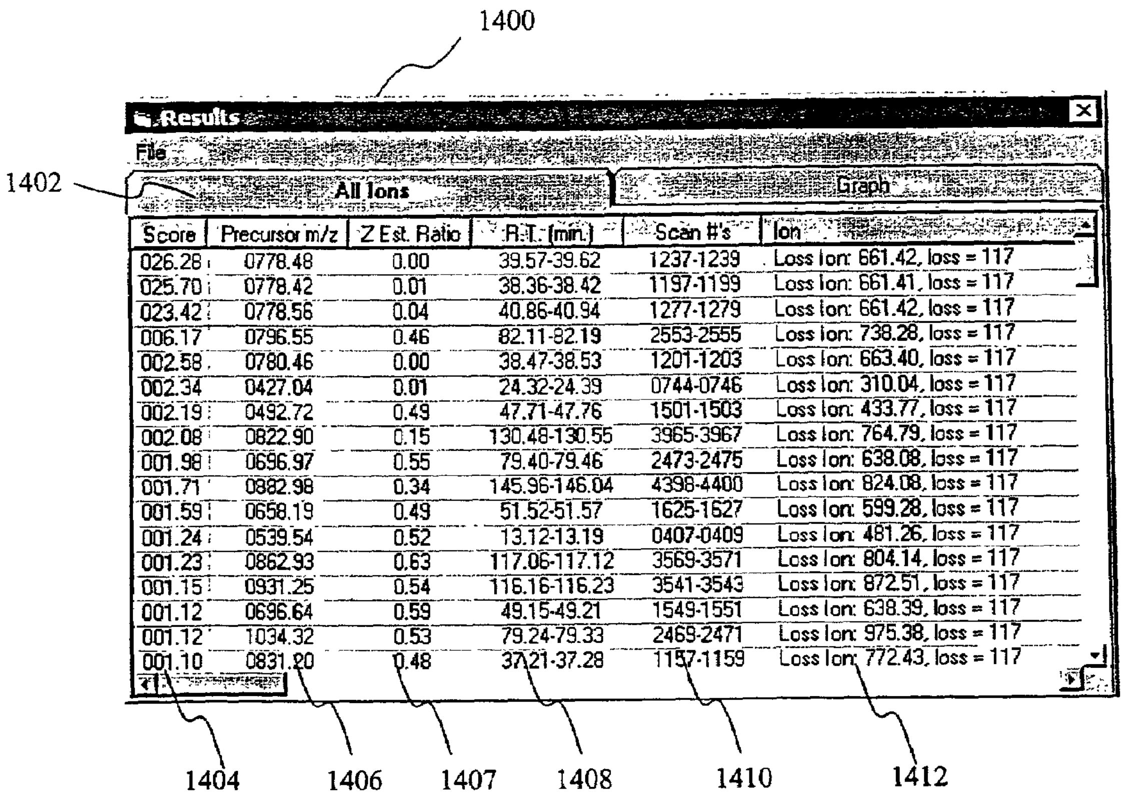
FIG. 14 shows a results window, which is part of the graphical user interface, used to display results of the mining of mass spectral data.

FIG. 14 shows an exemplary results window 1400 which displays mining results in tabular form upon selection of "All Ions" display 1402. The data displayed has columns for the scores 1404, precursor m/z 1406, charge estimation ratio 1407, retention time for the set of scans 1408, the scan numbers of the set of scans 1410, and the ions that matched the spectral characteristics and were scored 1412. The results are displayed according to descending scores 1404. However, the results may be sorted and displayed based on any of the columns. To designate the sort column, the user clicks on the chosen column title at the top of each column.

Figure 15:
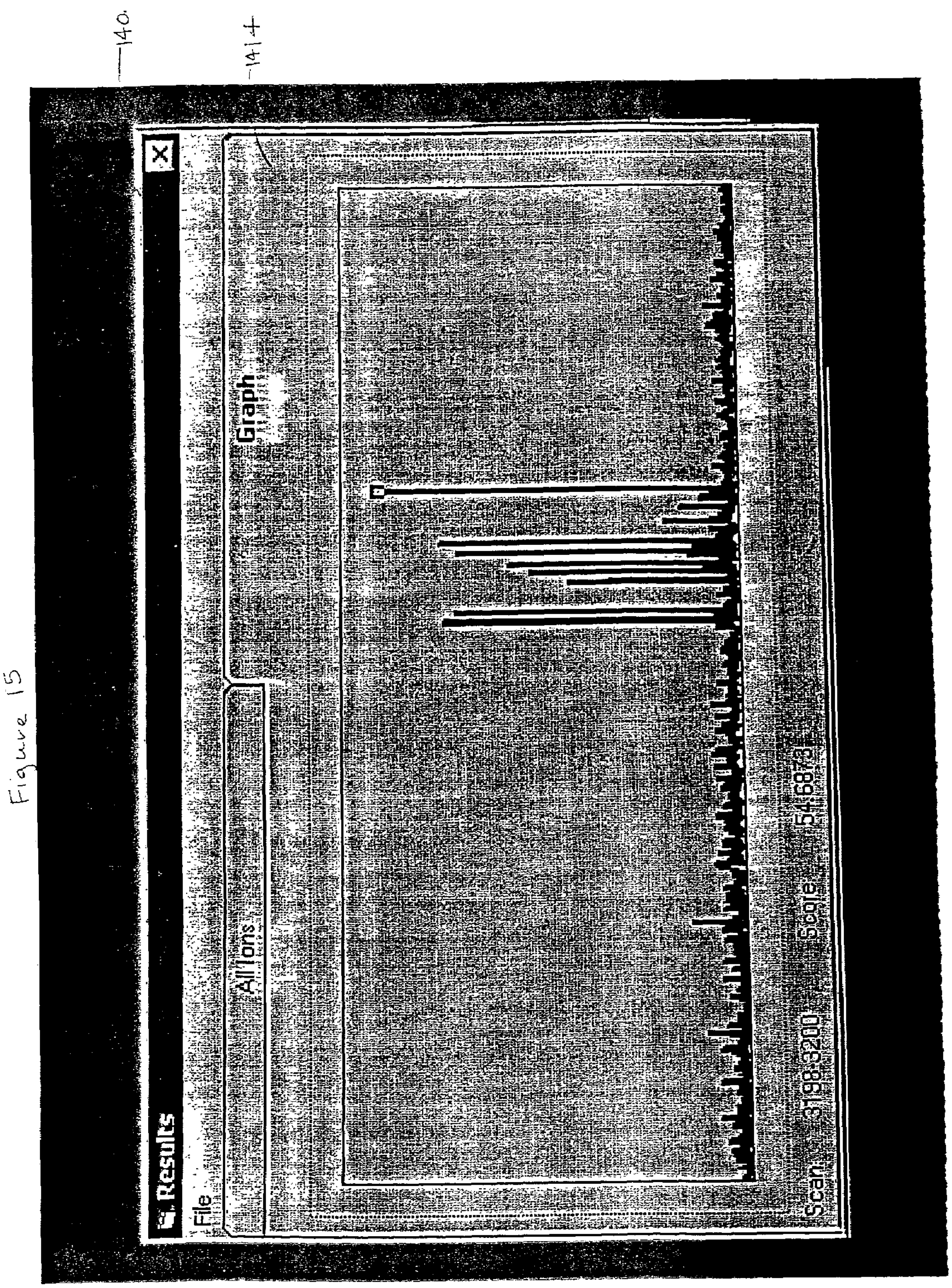
FIG. 15 shows the results window, which is part of the graphical user interface, used to display the results of the mining of mass spectral data in graphical form.

FIG. 15 shows the results window 1400 which displays the mining result in graphical form upon selection of "Graph" display 1414. The m/z is shown on the x-axis and the score is shown on the y-axis. A marker on its peak indicates the precursor m/z ion with the highest score.

Having generally described this invention, a further understanding can be obtained by reference to certain specific examples which are provided herein for purposes of illustration only and are not intended to be limiting unless otherwise specified.

Figure 16:
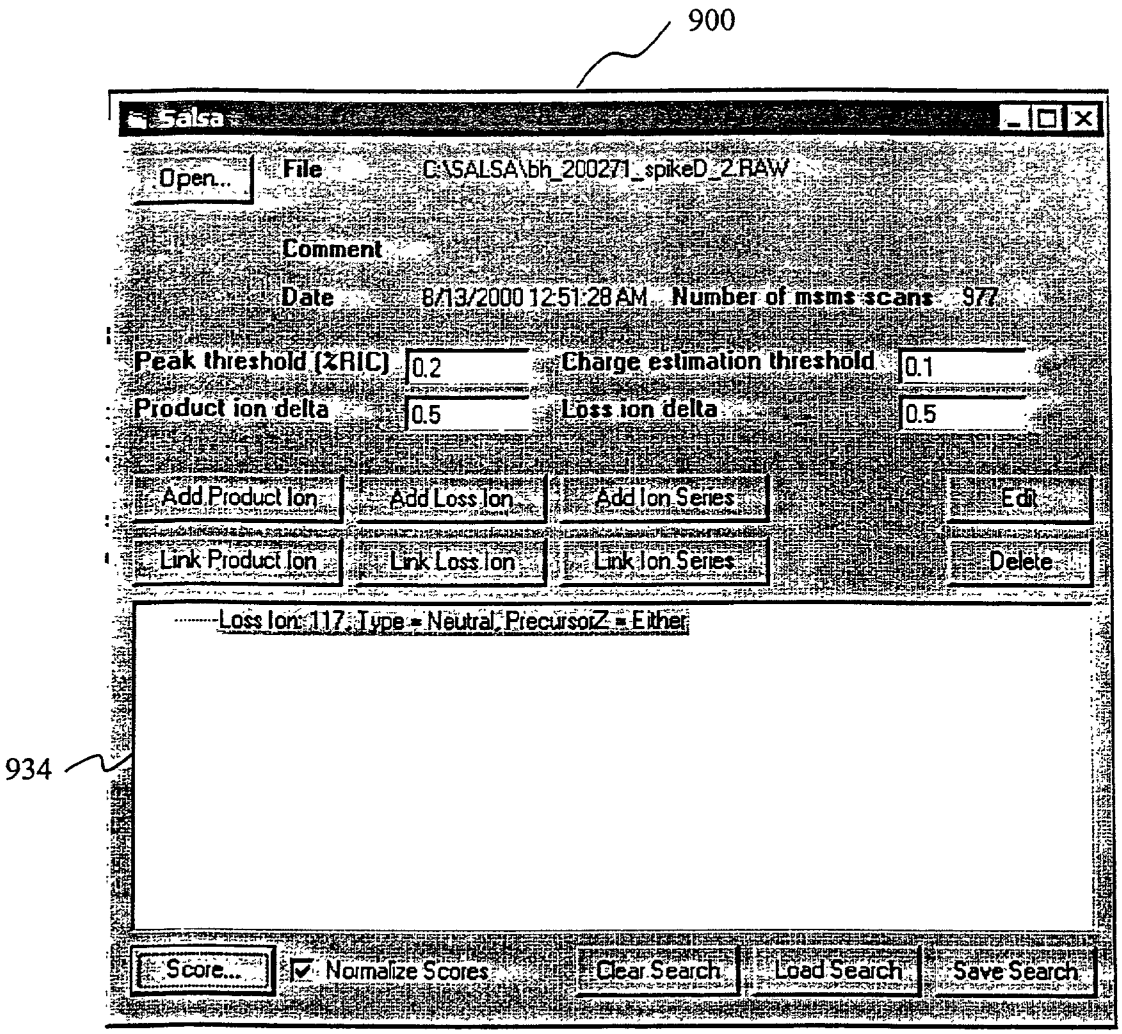
FIG. 16 shows an exemplary loss ion spectral characteristic used for mining mass spectral data.

In a first example, suppose that a pyrrole adduct on a peptide ion fragmented with a neutral loss of 117 Da due to loss of the pyrrole moiety. To mine a LC-MS-MS data file for MS—MS scans that display this loss ion feature, the user selects the Add Loss Ion button 920 in FIG. 9 and the loss ion parameter window 1100 in FIG. 11 appears. The user inputs "117" into the mass field 1102, clicks "Neutral" in the type of loss pull-down window 1104, and clicks "Either" in precursor charge pull-down window 1106. "Either" is chosen because a neutral loss may occur from either a singly- or doubly-charged precursor ion. The user then clicks the OK button 1108 and the control window 900 displays the specified characteristics in the window 934 as shown in FIG. 16. The user may either check or uncheck the Normalize Scores box 938 (depending on whether the user wishes to obtain normalized scores). Then, the user clicks the Score button 936 and the mining process runs.

FIG. 14 shows the results of the mining process in tabular form where the scores are listed in descending order. The top three scores are for scans that correspond to the desired peptide adduct, which has a precursor singly-charged m/z of 778 as shown in column 1406. The results indicate that three sets of MS—MS scans were recorded for this chemical species eluting in the LC-MS-MS analysis between 38.36 and 40.94 minutes. In each case, the charge estimation ratio (column 1407) indicates a ratio of less than 0.1, so that the spectrum is indicative of a singly charged species. The results also indicate from the "Ion" column 1412 that the spectrum has an intense ion at m/z 661, which is the product ion formed by loss of the neutral fragment.

Figure 17:
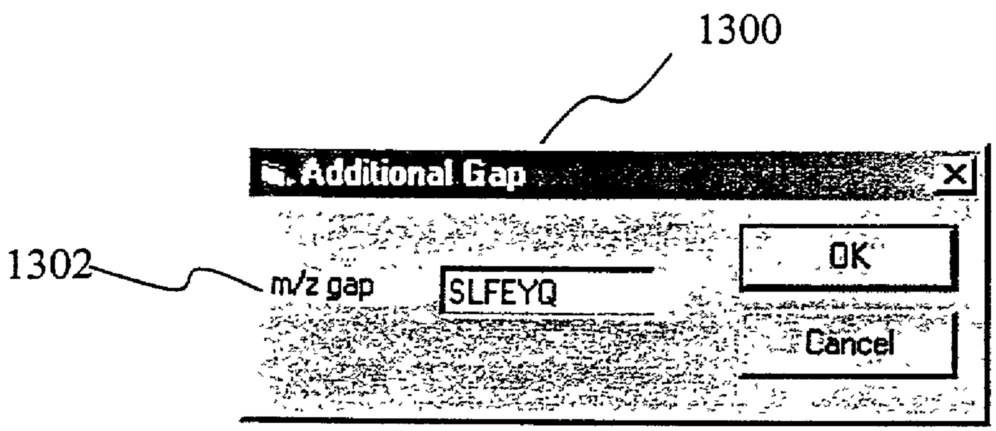
FIG. 17 shows an exemplary additional ion series gap used for mining mass spectral data.
Figure 18:
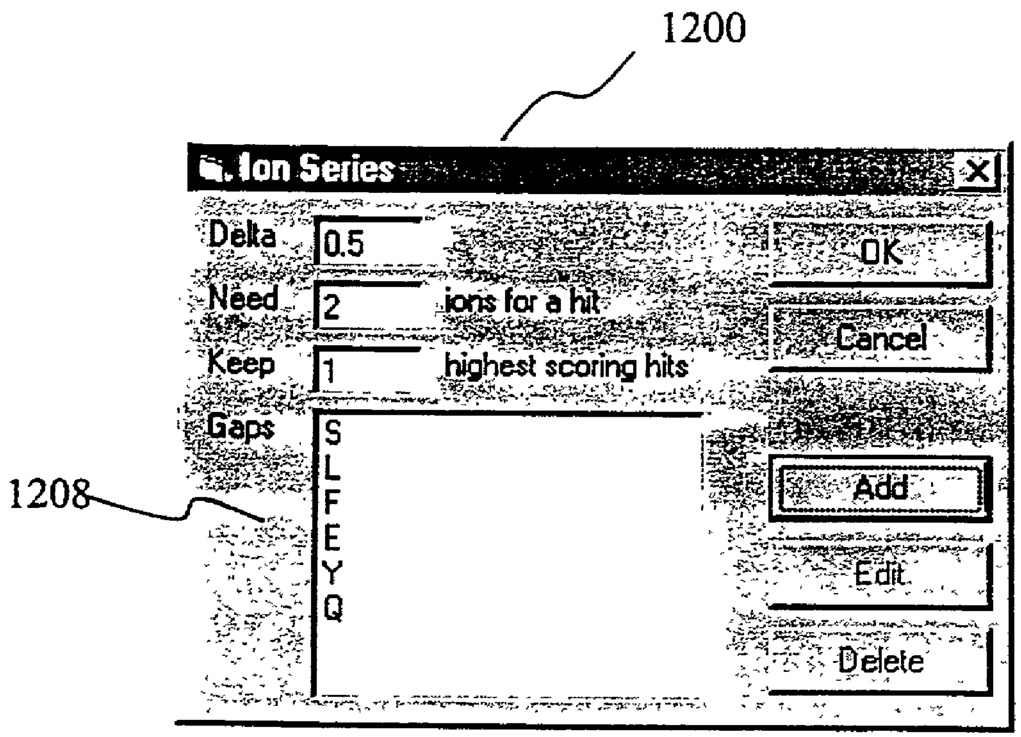
FIG. 18 shows an exemplary ion series parameter window in which the spectral characteristics have been specified.
Figure 19:
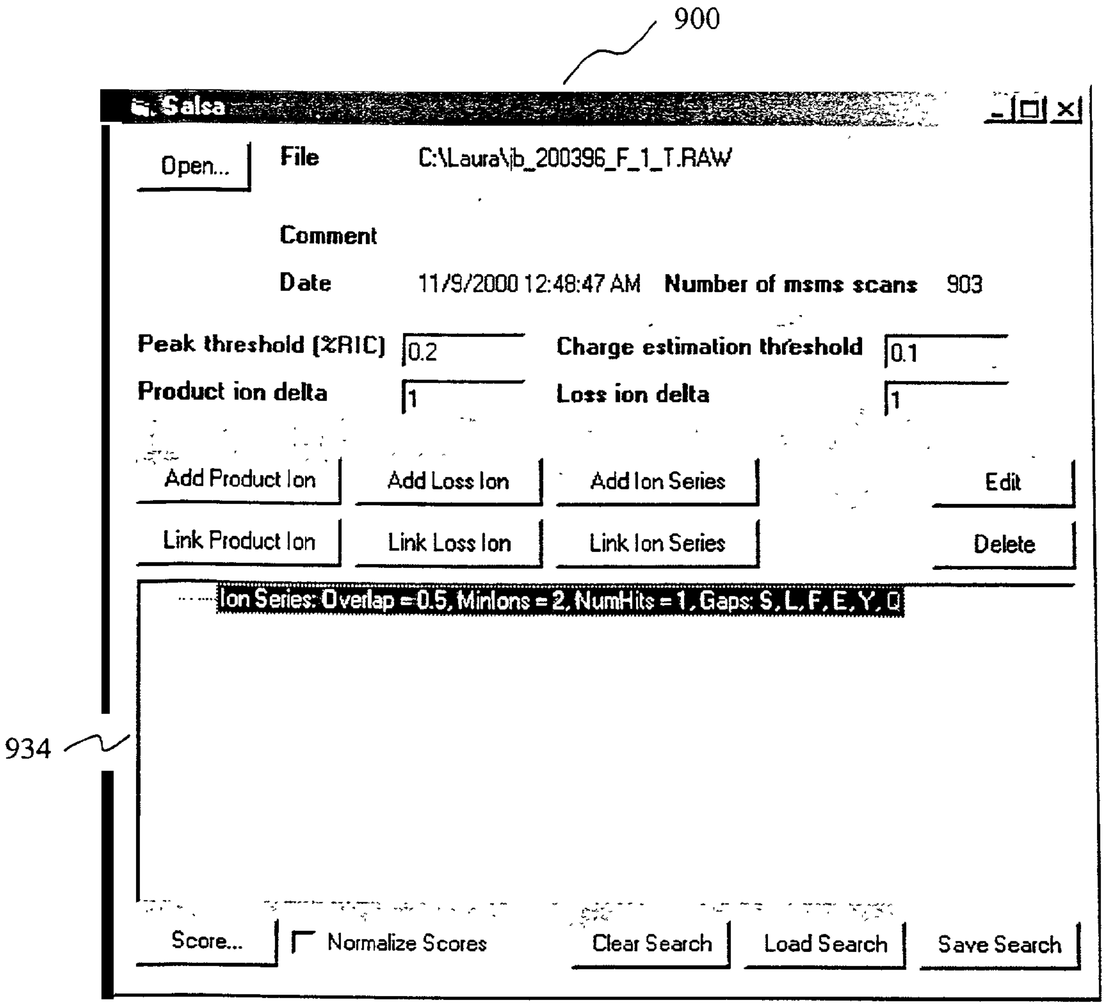
FIG. 19 shows an exemplary control window in which spectral characteristics have been specified.

In another example, suppose a sample of fibrinogen digested with trypsin contains the tryptic peptide NSLFEYQK. The search of the present invention can be performed using the inner amino acids from the peptide SLFEYQ. As such, the user specifies these inner amino acids as the ion series spectral characteristic to be mined to find MS—MS spectra of peptides containing this sequence motif or its variants. Accordingly, the user selects the Add Ion Series button 922 in FIG. 9 to input the ion series spectral characteristic. The ion series parameter window 1200 opens and the user specifies the threshold settings in field 1202, 1204, and 1206. The user then clicks the Add button 1214 in FIG. 12 and the parameter window 1300 of FIG. 13 opens to allow the user to add the m/z series parameter. As such, the user types the inner amino acid sequence SLFEYQ into the field 1302, as shown in FIG. 17. The user then clicks the OK button 1304 and the parameter window 1300 closes. Subsequently, the ion series parameter window 1200 appears with the spectral characteristics inputted in the window 1208 as shown in FIG. 18. If the series is correct, the user clicks the OK button 1210 and the ion series parameter window 1200 closes. Then, the ion series search criterion appear in the window 934 of the control window 900 as shown in FIG. 19. The ion series is the primary spectral characteristic.

When searching for a known peptide such as a tryptic peptide, the b- and y-ions for this peptide can be determined. So, the masses of these product ions can be added to an ion series search as a secondary search parameter to define the search.

Figure 20:
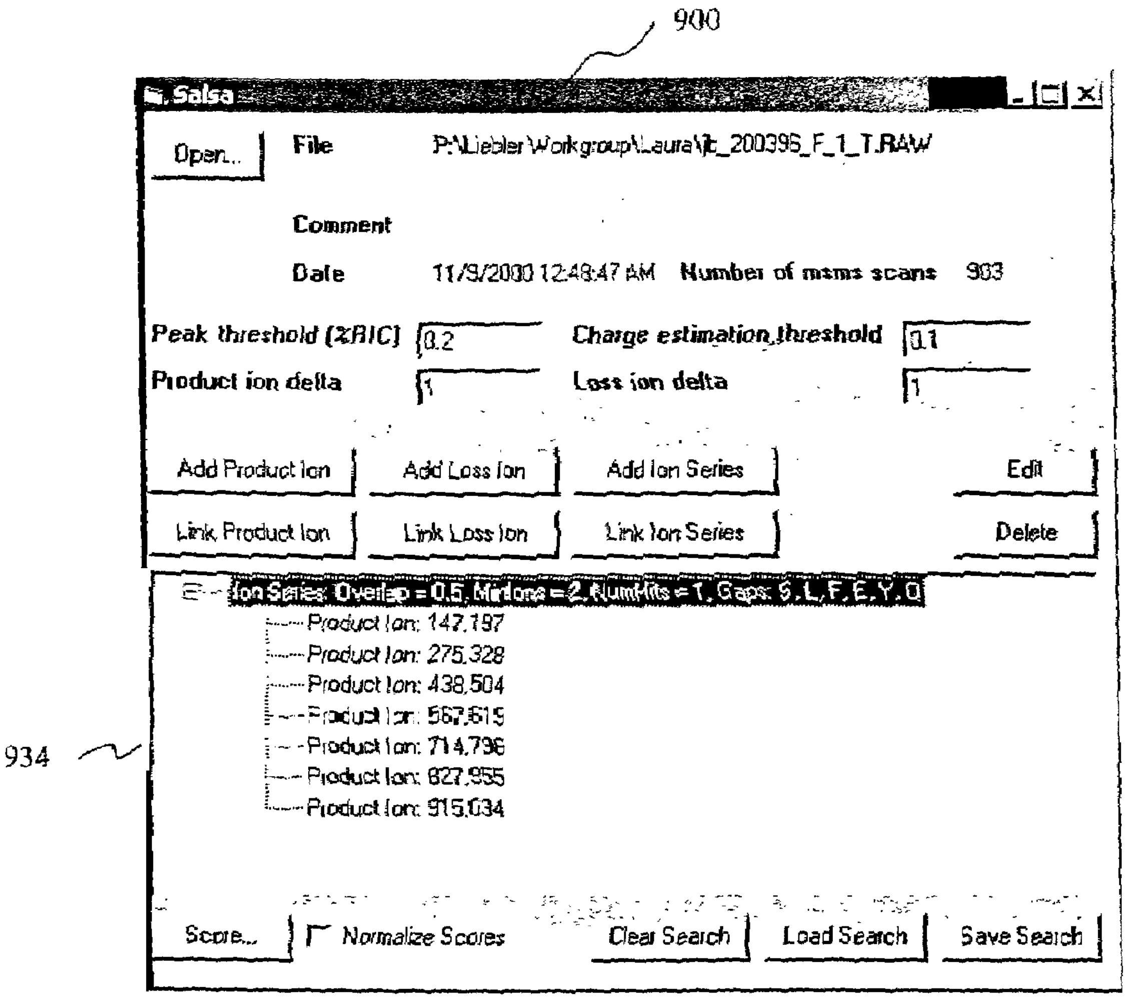
FIG. 20 shows an exemplary control window in which primary and secondary spectral characteristics have been specified.

Accordingly, the user wants to specify multiple product ion characteristics as secondary. The user highlights the ion series characteristic in the window 934 and then clicks the Link Product Ion button 924 to link product ion spectral characteristics to the ion series spectral characteristic. The product ion parameter window 1000 opens and the user specifies the product ion m/z value in field 1002 of FIG. 10. The user then clicks the OK button 1004 and the product ion secondary characteristic is entered. The user presses the Enter key on the keyboard, or any appropriate data entry device, and the product ion window 1000 reappears for the next product ion secondary characteristic entry. The process is the repeated until all the secondary product ion characteristics are specified. As shown in FIG. 20, the secondary values are listed below the primary spectral characteristic and indented. The user clicks on the score button and begins the search.

Figure 21:
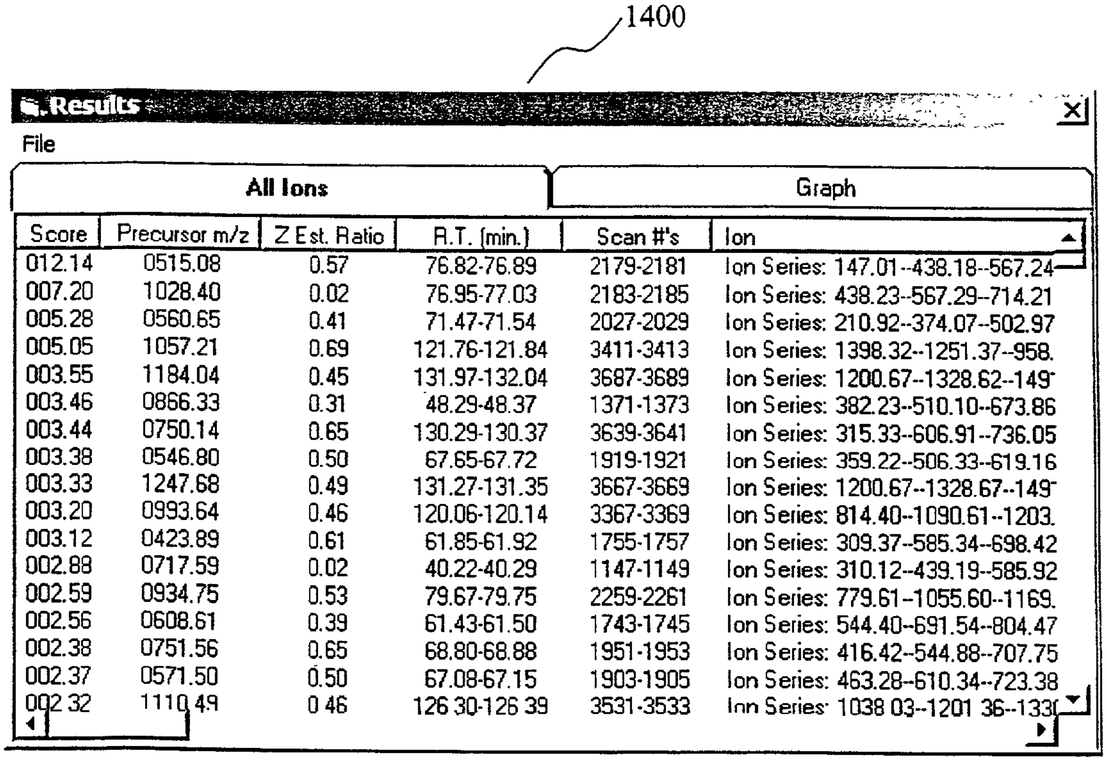
FIG. 21 shows an exemplary results window indicating the mass spectral data that match the spectral characteristics indicated in FIG. 20.

FIG. 21 shows the results of the search after hitting the score button. Again as discussed previously the six columns of data are shown in this example in tabular form. A high scoring scan is verified by checking that the ion score matches the expected y-ions for the peptide and that the mass of the precursor ion matches the expected peptide mass whether singly, doubly, or triply charged. Incomplete tryptic digestion can produce fragments that contain the peptide motif used in the search such that the mass will be larger than expected. If additional amino acids are at the c-terminus of the search peptide, the y-ion score will not match the expected y-ions. Therefore it should be considered to consider incomplete digestion when trying to determine identity of peptides with high values. In FIG. 21, the highest scoring scan (with the score 12.14), has the precursor m/z of 515.08, which corresponds to the doubly charged mass of the search peptide, NSLFEYQK. The second highest score 7.20 corresponds to the singly charged mass of the search peptide. Both of these scans contain fragment ions that correspond to the expected y-ions of the search peptide.

The mechanisms and processes set forth in the present description may be implemented using a conventional general purpose microprocessor programmed according to the teachings in the present specification, as will be appreciated to those skilled in a relevant art(s). Appropriate software coding can readily be prepared by skilled programmers based on the teachings of the present disclosure, as will also be apparent to those skilled in the relevant art(s).

The present invention thus also includes a computer-based product which may be hosted on a storage medium and include instructions which can be used to program a computer to perform a process in accordance with the present invention. This storage medium can include but is not limited to any type of disk including floppy disk, optical disk, CD-ROMs, magneto-optical disk, ROMs, RAMs, EPROMS, EEPROMS, flash memory, magnetic or optical cards, or any type of media suitable for storing electronic instructions.

It is to be understood that the structure of the software used to implement the invention may take on any desired form. For example, the mining method illustrated in FIGS. 4–8 may be implemented in a single program, multiple programs or routines or in any desired manner.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of United States is:

1. A method for mining mass spectra, comprising:

receiving primary spectral characteristics to be identified in a mass spectrum to be mined;

receiving secondary spectral characteristics associated with respective of said primary spectral characteristics;

searching said mass spectrum to be mined for matching portions which match said primary spectral characteristics;

when a match is found, searching said mass spectrum for subportions which match the secondary spectral characteristics associated with said primary spectral characteristics for which the match was found; and assigning scores to said subportions of said mass spectrum to be mined to indicate a degree of correlation between said subportions of said mass spectrum to be mined and said primary and secondary spectral characteristics.

2. The method of claim 1, wherein said mass spectrum is obtained by any one of dissociation and full-scan.

3. The method of claim 1, wherein the step of receiving primary spectral characteristics includes receiving at least one of a product ion, a loss ion, and an ion series.

4. The method of claim 3, wherein said step of receiving at least one of a product ion, a loss ion, and an ion series comprises specifying each of a product ion, a loss ion, and an ion series; and said assigning step includes:

calculating a product ion score;

calculating a loss ion score;

calculating an ion series score;

adjusting said product ion, loss ion, or said ion series score if respective said product ion, loss ion, or ion series spectral characteristic is secondary; and adding said product ion, loss ion, and ion series scores.

5. The method of claim 4, wherein the step of calculating a product ion score includes:

identifying a most abundant ion within a window around said product ion spectral characteristic; and setting said product ion score as a percentage of total ion current of said identified ion.

6. The method of claim 4, wherein the step of calculating a loss ion score includes:

calculating a loss ion mass per unit charge based on an actual precursor ion mass per unit charge and said loss ion spectral characteristic;

identifying a most abundant ion within a window around said calculated loss ion mass per unit charge; and setting said loss ion score as a percentage of total ion current of said identified ion.

7. The method of claim 4, wherein said step of calculating said ion series score includes:

specifying distances between ions in an ion series as the ion series spectral characteristic;

generating hypothetical ions separated by said specified distances;

aligning said mass spectrum with said hypothetical ions;

identifying most abundant ions within respective windows around said aligned mass spectrum at said specified distances; and setting said ion series score as a geometric mean of a percentage of total ion current of said identified ions, wherein said ion series score includes the following term $$N(I_1 \cdot I_2 \cdot I_3 \ldots \cdot In)^{1/n}$$

where N is a number of said identified ions that correspond to said hypothetical ions and $I_1$–$I_n$ are respective percentages of said total ion current of said identified ions.

8. The method of claim 4, wherein said adjusting step includes:

setting said secondary spectral characteristic score as a geometric mean of a primary spectral characteristic score and said secondary spectral characteristic score, wherein said secondary spectral characteristic score does not exceed said primary spectral characteristic score to which said secondary spectral characteristic score is linked.

9. The method of claim 1, wherein said step of receiving said secondary spectral characteristics includes linking said secondary spectral characteristics hierarchically with said primary spectral characteristics.

10. The method of claim 1, further comprising:

preprocessing said mass spectrum; and displaying said scores from said assigning step.

11. The method of claim 10, wherein said preprocessing step includes:

subtracting nonfragment ions from said mass spectrum;

estimating precursor charge of mass spectrum resulting from said subtracting step; and normalizing ion intensities of mass spectrum from said estimating step as a percentage of a total ion current.

12. The method of claim 10, wherein the displaying step includes displaying said scores in one of tabular and graphical form.

13. The method of claim 1, wherein the step of receiving said primary spectral characteristics includes automatically specifying said primary spectral characteristics based on said mass spectrum, and wherein the step of receiving said secondary spectral characteristics includes automatically specifying said secondary characteristics based on said mass spectrum.

14. The method of claim 1, further comprising:

adjusting control parameters of a device that produces said mass spectrum based on said assigned scores.

15. A computer readable medium containing program instructions for execution on a computer system, which when executed by the computer system, cause the computer system to perform the method recited in any one of claims 1 through 14.

16. A method for mining collision-induced dissociation (CID) spectra, comprising:

receiving primary spectral characteristics to be identified in a mass spectrum to be mined;

receiving secondary spectral characteristics associated with respective of said primary spectral characteristics;

searching said CID spectrum to be mined for matching portions which match said primary spectral characteristics;

when a match is found, searching said mass spectrum for subportions which match said secondary spectral characteristics associated with said primary spectral characteristics for which the match was found; and assigning scores to said subportions of said CD spectrum to be mined to indicate a degree of correlation between said subportions of said CID spectrum to be mined and said primary and secondary spectral characteristics.

17. The method of claim 16, wherein the step of receiving primary spectral characteristics includes receiving at least one of a product ion, a loss ion, and an ion series.

18. The method of claim 17, wherein said step of receiving at least one of a product ion, a loss ion, and an ion series comprises specifying each of a product ion, a loss ion, and an ion series; and said assigning step includes:

calculating a product ion score;

calculating a loss ion score;

calculating an ion series score;

adjusting said product ion, loss ion, or said ion series score if respective said product ion, loss ion, or ion series spectral characteristic is secondary; and adding said product ion, loss ion, and ion series scores.

19. The method of claim 18, wherein the step of calculating a product ion score includes:

identifying a most abundant ion within a window around said product ion spectral characteristic; and setting said product ion score as a percentage of total ion current of said identified ion.

20. The method of claim 18, wherein the step of calculating a loss ion score includes:

calculating a loss ion mass per unit charge based on an actual precursor ion mass per unit charge and said loss ion spectral characteristic;

identifying a most abundant ion within a window around said calculated loss ion mass per unit charge; and setting said loss ion score as a percentage of total ion current of said identified ion.

21. The method of claim 18, wherein said step of calculating said ion series score includes:

specifying distances between ions in an ion series as the ion series spectral characteristic;

generating hypothetical ions separated by said specified distances;

aligning said CID spectrum with said hypothetical ions;

identifying most abundant ions within respective windows around said aligned CID spectrum at said specified distances; and setting said ion series score as a geometric mean of a percentage of total ion current of said identified ions, wherein said ion series score includes the following $$N(I_1 \cdot I_2 \cdot I_3 \ldots \cdot In)^{1/n}$$

where N is a number of said identified ions that correspond to said hypothetical ions and $I_1$–$I_n$ are respective percentages of said total ion current of said identified ions.

22. The method of claim 18, wherein said adjusting step includes:

setting said secondary spectral characteristic score as a geometric mean of a primary spectral characteristic score and said secondary spectral characteristic score, wherein said secondary spectral characteristic score does not exceed said primary spectral characteristic score to which said secondary spectral characteristic score is linked.

23. The method of claim 16, wherein said step of receiving primary spectral characteristics includes linking said secondary spectral characteristic hierarchically with said primary spectral characteristic.

24. The method of claim 16, further comprising:

preprocessing said CID spectrum; and displaying said scores from said assigning step.

25. The method of claim 24, wherein said preprocessing step includes:

subtracting nonfragment ions from said CID spectrum;

estimating a precursor charge of said CID spectrum resulting from said subtracting step; and normalizing ion intensities of said CID spectrum from said estimating step as a percentage of a total ion current.

26. The method of claim 24, wherein the displaying step includes displaying said scores in one of tabular and graphical form.

27. The method of claim 16, wherein the step of specifying spectral characteristics includes automatically specifying said spectral characteristics based on said CID spectrum, and wherein the step of specifying a relationship includes automatically specifying said relationship based on said CID spectrum.

28. The method of claim 16, further comprising:

adjusting control parameters of a device that produces said CID spectrum based on said assigned scores.

29. A system for mining mass spectra, comprising:

means for receiving said primary spectral characteristics to be identified in said mass spectrum to be mined and for receiving said secondary spectral characteristics associated with respective of said primary spectral characteristics;

means for searching said mass spectrum to be mined for matching portions which match said primary spectral characteristics, and when a match is found, searching said mass spectrum for subportions which match the secondary spectral characteristics associated with said primary spectral characteristics for which the match was found; and means for assigning scores to said subportions of said mass spectrum to be mined to indicate a degree of correlation between said subportions of said mass spectrum to be mined and said primary and secondary spectral characteristics.

30. The system of claim 29, wherein said mass spectrum is obtained by any one of dissociation and full-scan.

31. The system of claim 29, further comprising:

means for preprocessing said mass spectrum; and means for displaying said scores from said assigning means.

32. The system of claim 29, wherein the means for receiving said primary spectral characteristics includes means for automatically specifying said primary spectral characteristics based on said mass spectrum, and wherein the means for receiving said secondary spectral characteristics includes means for automatically specifying said secondary spectral characteristics based on said mass spectrum.

33. The system of claim 29, further comprising:

means for adjusting control parameters of a device that produces said mass spectrum based on said assigned scores.

34. A system, comprising:

an input mechanism for a user to input primary spectral characteristics to be identified in a mass spectrum to be mined and for said user to input secondary spectral characteristics associated with respective of said primary spectral characteristics;

a memory device having embodied therein a mass spectrum to be mined; and a processor in communication with the memory device and the input mechanism, the processor configured to receive from said input mechanism said primary spectral characteristics to be identified in said mass spectrum to be mined, receive from said input mechanism said secondary spectral characteristics associated with respective of said primary spectral characteristics, search said mass spectrum to be mined for matching portions which match said primary spectral characteristics, when a match is found, search said mass spectrum for subportions which match the secondary spectral characteristics associated with said primary spectral characteristics for which the match was found, and assign scores to said subportions of said mass spectrum to be mined to indicate a degree of correlation between said subportions of said mass spectrum to be mined and said primary and secondary spectral characteristics.

35. A computer program product including a computer readable medium storing instructions for mining mass spectrum, which when executed by the computer results in the computer performing steps comprising:

receiving from a graphical user interface primary spectral characteristics to be identified in a mass spectrum to be mined;

receiving from said graphical user interface secondary spectral characteristics associated with respective of said primary spectral characteristics;

searching said mass spectrum to be mined for matching portions that match said primary spectral characteristics, when a match is found, searching said mass spectrum for subportions which match the secondary spectral characteristics associated with said primary spectral characteristics for which the match was found, and assigning scores to said subportions of said mass spectrum to be mined to indicate a degree of correlation between said subportions of said mass spectrum to be mined and said primary and secondary spectral characteristics.

36. The computer program product of claim 35, wherein said mass spectrum are obtained by any one of dissociation and full-scan.

37. The computer program product of claim 35, wherein the graphical user interface code is configured to accept at least one of a product ion, a loss ion, and an ion series as an input, identify said primary spectral characteristics as being one of a primary and a secondary spectral characteristic, and link said secondary spectral characteristic with said primary spectral characteristic such that said secondary spectral characteristic is detected only after said primary spectral characteristic is detected.

38. The computer program product of claim 35, wherein the graphical user interface code comprises:

a control window configured to input the primary and secondary spectral characteristics; and a results window configured to display said scores of said mass spectrum.

39. The computer program product of claim 38, wherein the graphical user interface code further comprises:

a product ion window configured to input said product ion spectral characteristic;

a loss ion window configured to input said loss ion spectral characteristic; and an ion series window configured to input said ion series spectral characteristic, wherein said product ion, loss ion, and ion series windows open when respective said spectral characteristics are selected in said control window.

40. The computer program product of claim 38, wherein said results window displays said scores in one of tabular and graphical form.

41. The computer program product of claim 35, wherein said at least one of a product ion, a loss ion, and an ion series comprises each of a product ion, a loss ion, and an ion series; and the mining code is configured to calculate a product ion score, calculate a loss ion score, calculate an ion series score, adjust said product ion, loss ion, or said ion series score if respective said product ion, loss ion, or ion series spectral characteristic is secondary, wherein said secondary spectral characteristic score does not exceed said primary spectral characteristic score to which said secondary spectral characteristic score is linked, and add said product ion, loss ion, and ion series scores.

42. The computer program product of claim 41, wherein said mining code is further configured to calculate the product ion score by identifying a most abundant ion within a window around said product ion spectral characteristic and setting said product ion score as a percentage of total ion current of said identified ion, calculate the loss ion score by calculating a loss ion mass per unit charge based on an actual precursor ion mass per unit charge and said loss ion spectral characteristic, identifying a most abundant ion within a window around said calculated loss ion mass per unit charge, and setting said loss ion score as a percentage of total ion current of said identified ion, and calculate the ion series score by specifying distances between ions in an ion series as the ion series spectral characteristic, generating hypothetical ions separated by said specified distances, aligning said mass spectrum with said hypothetical ions, identifying most abundant ions within respective windows around said aligned mass spectrum at said specified distances, and setting said ion series score as a geometric mean of a percentage of total ion current of said identified ions, wherein said ion series score includes the following $$N(I_1 \cdot I_2 \cdot I_3 \ldots \cdot In)^{1/n}$$

where N is a number of said identified ions that correspond to said hypothetical ions and $I_1$–$I_n$ are respective percentages of said total ion current of said identified ions.

43. The computer program product of claim 35, further comprising:

a preprocessing code configured to process said mass spectrum prior to mining in order to remove spurious mass spectra data.

44. The computer program product of claim 43, wherein the preprocessing code is configured to subtract nonfragment ions from said mass spectrum, estimate a precursor charge of said mass spectrum resulting from said subtracting step, and normalize an ion intensity of said mass spectrum from said estimating step as a percentage of a total ion current.

45. The computer program product of claim 35, wherein the graphical user interface code is configured to accept automatically specified said spectral characteristics and said relationship based on said mass spectrum.

46. The computer program product of claim 35, further comprising:

a control code configured to adjust control parameters of a device which generates said mass spectrum based on said assigned scores.

47. A graphical user interface, comprising:

a control window configured to accept an input from a user, the input including primary spectral characteristics to be identified in a mass spectrum to be mined and secondary spectral characteristics associated with respective of said primary spectral characteristics; and a results window configured to display scores of portions of said mass spectrum to be mined indicating a correlation between said mass spectrum portions and said primary and secondary spectral characteristics based on searching said mass spectrum for matching portions which match said primary spectral characteristics, and when a match is found, searching said mass spectrum for subportions which match said secondary spectral characteristics associated with respective of said primary spectral characteristics for which the match was found.

48. The graphical user interface of claim 47, wherein said results window displays said scores in one of tabular and graphical form.

* * * * *